US006936628B2

(12) United States Patent
Lee

(10) Patent No.: US 6,936,628 B2
(45) Date of Patent: *Aug. 30, 2005

(54) ORAL ADMINISTRATION OF EPOTHILONES

(75) Inventor: Francis Y. F. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/404,324

(22) Filed: Apr. 1, 2003

(65) Prior Publication Data

US 2003/0220378 A1 Nov. 27, 2003

Related U.S. Application Data

(60) Provisional application No. 60/370,104, filed on Apr. 4, 2002.

(51) Int. Cl.[7] .................... A61K 31/425; C07D 277/30
(52) U.S. Cl. ................ 514/365; 514/183; 514/366; 514/450; 548/202; 548/203; 548/204
(58) Field of Search ...................... 514/365, 183, 514/366, 450; 548/202–204

(56) References Cited

U.S. PATENT DOCUMENTS

| | | | |
|---|---|---|---|
| 6,194,181 B1 | 2/2001 | Hofmann et al. | |
| 6,204,388 B1 | 3/2001 | Danishefsky et al. | |
| 6,211,412 B1 | 4/2001 | Georg et al. | |
| 6,242,469 B1 | 6/2001 | Danishefsky et al. | |
| 6,262,094 B1 | 7/2001 | Hoefle et al. | |
| 6,316,630 B1 | 11/2001 | Danishefsky et al. | |
| 6,365,749 B1 | 4/2002 | Kim et al. | |
| 6,369,234 B1 | 4/2002 | Danishefsky et al. | |
| 6,380,227 B1 | 4/2002 | Mutz | |
| 6,380,394 B1 | 4/2002 | Nicolaou et al. | |
| 6,518,421 B1 | 2/2003 | Li et al. | |
| 6,576,651 B2 * | 6/2003 | Bandyopadhyay et al. | 514/365 |
| 6,605,599 B1 | 8/2003 | Vite et al. | |
| 6,686,380 B2 | 2/2004 | Lee | |
| 6,727,276 B2 | 4/2004 | Lee | |
| 6,780,620 B1 | 8/2004 | Li et al. | |
| 2003/0073677 A1 | 4/2003 | Lee | |
| 2003/0187039 A1 | 10/2003 | Favreau et al. | |
| 2003/0220295 A1 | 11/2003 | Vite et al. | |
| 2004/0214871 A1 | 10/2004 | Lee | |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | WO 00/039276 | 7/2000 |
| WO | 00/49021 | 8/2000 |
| WO | 00/66589 | 11/2000 |

OTHER PUBLICATIONS

Balog, A. et al., Angew, Chem. Int. Engl. 35, No. 23–24, pp. 2801–2803, 1996.*

Balog, A., et al., "Total Synthesis of (–)-Epothilone A", *Angew. Chem. Int. Ed. Engl.*, vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothilones, A New Class of Microtubule–stabilizing Agents with a Taxol–like Mechanism of Action", *Cancer Res.* 55, No. 11, 2325–2333 (1995).

Fujisawa, T., et al., "Deoxygenation of Epoxides to Olefins with FeCl$_3$–n–BuLi System", *Chem. Lett.*, 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).

(Continued)

Primary Examiner—Dwayne Jones
(74) Attorney, Agent, or Firm—Rena Patel; Anastasia P. Winslow; Gary D. Greenblatt

(57) ABSTRACT

The invention relates to methods of increasing the bioavailability of orally administered epothilones. Epothilones administered by the methods of the invention are sufficiently bioavailable to have a pharmacological effect. The invention further relates to pharmaceutical compositions, pharmaceutical dosage forms, and kits for use in the methods of the invention.

64 Claims, 7 Drawing Sheets

OTHER PUBLICATIONS

Gladysz, J. A., et al., "Deoxygenation of Epoxides by Metal Atom Cocondensation", *J. Org. Chem.,* vol. 41, No. 22, 3647–3648 (1976).

Hofle, G., et al., "Epothilone A and B—Novel 16-Membered Macrolides with Cytotoxic Activity: Isolation, Crystal Structure, and Conformation in Solution", *Angew. Chem. Int. Ed. Engl.,* vol. 35, No. 13/14, 1567–1569 (1996).

Hofle, G., et al., "N–Oxidation of Epothilone A–C and O–Acyl Rearrangement to C–19 and C–21 –Substituted Epothilones", *Angew. Chem. Int. Ed.,* vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett,* No. 6, 510–512 (1992).

Kowalski, R. J., et al., "Activities of the Microtubule–stabilizing Agents Epothilones A and B with Purified Tubulin and in Cells Resistant to Paclitaxel (Taxol®)" *J. Biol. Chem.,* vol. 272, No. 4, 2534–2541 (1997).

Kupchan, S. M., et al., "Reductive Elimination of Epoxides to Olefins with Zinc–Copper Couple", *J. Org. Chem.,* vol. 36, No. 9, 1187–1190 (1971).

Martin, M. G., et al., "Epoxides as Alkene Protecting Groups. A Mild and Efficient Deoxygenation", *Tetrahedron Letters,* vol. 25, No. 3, 251–254 (1984).

McMurry, J. E., et al., "Reduction of Epoxides to Olefins with Low Valent Titanium", *J. Org. Chem.,* vol. 40, No. 17, 2555–2556 (1975).

McMurry, J. E., et al., "Some Deoxygenation Reactions with Low–Valent Titanium ($TiCl_3/LiAlH_4$)", *J. Org. Chem.,* vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.,* vol. 119, No. 11, 2733–2734 (1997).

Nicolaou, K. C., et al., "An Approach to Epothilones Based on Olefin Metathesis", *Angew. Chem. Int. Ed. Engl.,* vol. 35, No. 20, 2399–2401 (1996).

Nicolaou, K. C., et al., "Total Synthesis of Epothilone A: The Macrolactonization Approach", *Angew. Chem. Int. Ed. Engl.,* vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.,* vol. 36, No. 19, 2097–2103 (1997).

Nicolaou, K.C., et al., "The Olefin Metathesis Approach to Epothilone A and Its Analogues", *J. Am. Chem. Soc.,* vol. 119, No. 34, 7960–7973 (1997).

Nicolaou, K. C., et al., "Total Syntheses of Epothilones A and B via a Macrolactonization–Based Strategy", *J. Am. Chem. Soc.,* vol. 119, No. 34, 7974–7991 (1997).

Nicolaou, K. C., et al., "Synthesis of Epothilones A and B in Solid and Solution Phase", *Nature,* vol. 387, 268–272 (1997).

Nicolaou, K. C., et al., "Synthesis of Epothilones A and B in Solid and Solution Phase" (Correction to *Nature* 387, 268–272 (1997), *Nature,* 390, 100 (1997).

Raucher, S., et al., "Total Synthesis of (+)–Dihydrocostunolide via Tandem Cope–Claisen Rearrangement", *J. Org. Chem.,* vol. 51, No. 26, 5503–5505 (1986).

Sato, M, et al., "Reduction of Organic Compounds with Low–Valent Niobium ($NbCl_5/NaAlH_4$)", *Chem. Letters,* 157–160 (1982).

Schinzer, D., et al., "Total Synthesis of (–)–Epothilone A", *Angew. Chem. Int. Ed. Engl.,* vol. 36, No. 5, 523–524 (1997).

Schobert, R., et al., "Reduction and Isomerization of Oxiranes and α–Diazoketones by Various Early Transition Metallocenes", *Synlett,* vol. 8, 465–466 (1990).

Sharpless, K. B., et al., "Lower Valent Tungsten Halides. A New Class of Reagents for Deoxygenation of Organic Molecules", *J. Amer. Chem. Soc.,* vol. 94, No. 18, 6538–6540 (1972).

Su, D.-S., et al., "Total Synthesis of (–)–Epothilone B: An Extension of the Suzuki Coupling Method and Insights into Structure–Activity Relationships of the Epothilones", *Angew. Chem. Int Ed. Engl.,* vol. 36, No. 7, 757–759 (1997).

Su, D.-S., et al., "Structure–Activity Relationships of the Epothilones and the First In Vivo Comparison with Paclitaxel", *Angew. Chem. Int. Ed. Engl.,* vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.,* vol. 6., No. 7, 893–898 (1996).

Winkler, J. D., et al., "A Model For The Taxol (Paclitaxel)/Epothilone Pharmacophore", *Boorg. Med. Chem. Letts.,* vol. 6, No. 24, 2963–2966 (1996).

Yang, Z., et al., "Total Synthesis of Epothilone A: The Olefin Metathesis Approach", *Angew. Chem. Int. Ed. Engl.,* vol. 36, No. 1/2, 166–168 (1997).

Bollag, D., et al., "Epothilone, A New Structural Class of Microtubule Stabilizer", Abstract, *Proc. Am. Assoc. Cancer Res.,* vol. 36, 86 Meet. 454 (1995).

Bollag, D., "Epothilones: Novel Microtubule–Stabilising Agents", *Expert Opin. Invest. Drugs,* vol. 6, No. 7, 867–873 (1997).

Bertinato, P., et al., "Studies Toward a Synthesis of Epothilone A: Stereocontrolled Assembly of the Acyl Region and Models for Macrocylization", J. Org. Chem., vol. 61, No. 23, 8000–8001 (1996).

*Chemical & Engineering News,* "Epothilone Epiphany: Total Syntheses", vol. 74, No. 52, 24–26 (1996).

*Chemical & Engineering News,* "First Total Synthesis of Epothilone B", vol. 75, No. 13, 23 (1997).

*Chemical & Engineering News,* "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.,* vol. 38, No. 8, 1359–1362 (1997).

De Brabander, J., et al., "Towards a Synthesis of Epothilone A: Rapid Assembly of the C1–C6 and C7–C12 Fragments", *Synlett,* vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.,* vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics,* vol. 49, No. 6, 560–563 (1996).

Marshall, A., "Total Synthesis of Epothilone", *Nature Biotechnology,* vol. 15, No. 3, 205 (1997).

Meng, D., et al., "Studies Toward a Synthesis of Epothilone A: Use of Hydropyran Templates for the Managment of Acyclic Stereochemical Relationships", *J. Org. Chem.,* vol. 61, No. 23, 7998–7999 (1996).

Meng, D., et al., "Total Syntheses of Epothilones A and B", *J. Am. Chem. Soc.,* vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.,* vol. 339, No. 1, 96–97 (1997).

Mulzer, J. and Mantoulidis, A., "Synthesis of the C(1)–C–(9) Segment of the Cytotoxic Macrolides Epothilon A and B", *Tetrahedron Lett.,* vol. 37, No. 51, 9179–9182 (1996).

Nicolaou, K, et al., "Chemistry, Biology and Medicine of Selected Tubulin Polymerizing Agents", *Pure Appl. Chem.,* vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.,* vol. 7, No. 5, 665–697 (1999).

Schinzer, D., et al., "Studies Towards the Total Synthesis of Epothilones: Asymmetric Synthesis of the Key Fragments", *Chem. Eur. J.,* vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.,* vol. 38, No. 12, 2061–2064 (1997).

Schinzer, D., et al., "Syntheses of (–)–Epothilone A", *Chem. Eur. J.,* vol. 5, No. 9, 2483–2491 (1999).

Schinzer, D., et al., "Syntheses of (–)–Epothilone B", *Chem. Eur. J.,* vol. 5, No. 9, 2492–2500 (1999).

Nicolaou, K. C., "Synthesis and Biological Properties of C12,13–Cyclopropylepothilone A and Related Epothilones", *Chemistry & Biology,* vol. 5, No. 7, 365–372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84–87 (1998).

Nicolaou et al., "Total Synthesis of Oxazole– and Cyclopropane–Containing Epothilone B Analogues by the Macrolactonization Approach", Chemistry, European Journal, vol. 3, No. 12, 1971–1986 (1997).

Nicolaou et al., "Chemical Biology of Epothilones", Angew, Chem. Int. Ed., 37, 2014–2045 (1988).

* cited by examiner

Cytotoxicity spectrum of BMS-310705 versus a panel of eight tumor cell lines). Bar graphs, on the right, depict the $IC_{50}$ values of the cell lines listed on the left hand column (top to bottom).

Figure 2

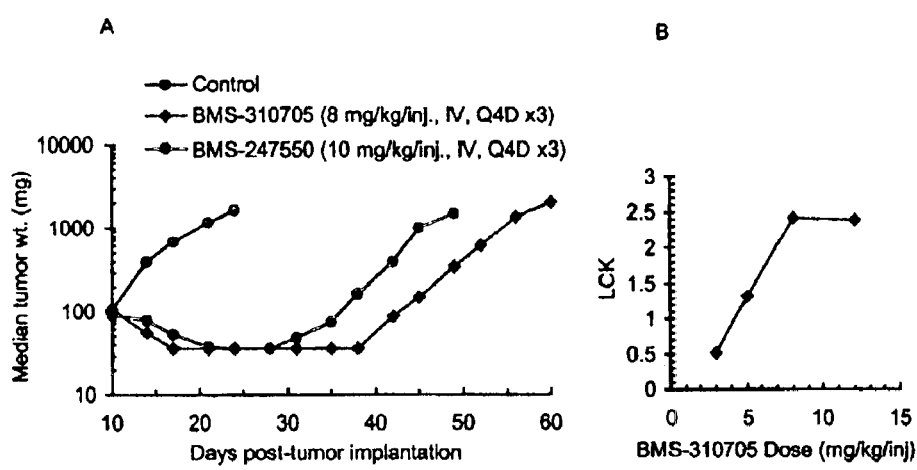

Figure 2(A) Comparative antitumor activity of IV BMS-310705 and IV BMS-247550 in the Pat-7 human ovarian carcinoma model. Compound was administered at the indicated doses, every 4 days for a total of 3 administrations starting 10 days after tumor implantation Q4D x3;10). Each datum point represents the median tumor weight of 8 mice.

Figure 2(B) Dose-response relationship for BMS-310705 in the Pat-7 tumor model.

Comparative antitumor activity of oral BMS-310705 and IV BMS-247550 versus the A2780Tax human ovarian carcinoma model. Compound was administered at the indicated doses, every 4 days for a total of 3 administrations starting 13 days after tumor implantation Q4D x3;13). Each datum point represents the median tumor weight of 8 mice.

Comparative antitumor activity of oral BMS-310705 and IV BMS-247550 in the Pat-7 human ovarian carcinoma model. Compound was administered at the indicated doses, every 4 days for a total of 3 administrations starting 10 days after tumor implantation Q4D x3;10). Each datum point represents the median tumor weight of 8 mice.

Figure 5(A) Effects of various infusional doses of BMS-310705 on sc Pat-7 tumor growth. BMS-310705 was administered by infusion over a 10-hr period, 5% of the dose was given as loading dose.

Figure 5(B) Plasma BMS-310705 concentrations following infusional treatment with BMS-310705 at various doses. Error bars represent 1 S.D.

FIGURE 6 (A)

| Document Control No. | Route[a] | Dose (mg/kg) | N size[b] | Formulation[c] | CMAX (ng/mL) | AUC (h.ng/mL) | CLT (mL/min/kg) | VSS (L/kg) | T-HALF (h) | F (%) |
|---|---|---|---|---|---|---|---|---|---|---|
| | | | | | | MOUSE | | | | |
| 920008300 | IV | 5 | 3[d] | Cremophor:ethanol:water (10:10:80) | 298 | 547 | 152 | 38 | 3.3 | n.a.[e] |
| | Oral | 15 | 3[d] | Cremophor:ethanol:phosphate buffer (10:10:80) | 180 | 343 | n.a. | n.a. | 3.3 | 21 |
| | | | | | | RAT | | | | |
| 920008300 | IA | 2 | 2m | Ethanol:water (10:90) | 404 | 133[f] | n.d.[g] | n.d. | n.d. | n.a. |
| | IA | 2 | 2m | Cremophor:ethanol:water (10:10:80) | 672 | 708[f] | n.d. | n.d. | n.d. | n.a. |
| | IA | 2 | 2m | Propylene glycol:ethanol:water (40:5:55) | 583 | 210[f] | n.d. | n.d. | n.d. | n.a. |
| | Oral | 8 | 2m | Propylene glycol:ethanol:phosphate buffer (58:12:30) | 147 | 237[f] | n.a. | n.a. | n.d. | 28[h] |
| 920008300 | IA | 2 | 3m | Cremophor:ethanol:water (10:10:80) | 803 | 2889[i] | n.d. | n.d. | n.d. | n.a. |
| | IA | 2 | 3m | Ethanol:phosphate buffer (6:94) | 634 | 717[i] | n.d. | n.d. | n.d. | n.a. |
| | Oral | 8 | 3m | Ethanol:phosphate buffer (18:82) | 442 | 977[i] | n.d. | n.a. | n.d. | 34[j] |
| 920008982 | IV | 1 | 3m<br>3f | 50 mM citrate buffer (pH 5) | 205<br>183 | 204<br>159 | n.d. | n.d. | n.d. | n.a. |
| | IV | 5 | 3m<br>3f | 50 mM citrate buffer (pH 5) | 2058<br>2094 | 859<br>1272 | n.d. | n.d. | n.d. | n.a. |
| | IV | 7 | 3m<br>3f | 50 mM citrate buffer (pH 5) | 3914<br>3507 | 1587<br>1938 | n.d. | n.d. | n.d. | n.a. |

FIGURE 6 (B)

| Document Control No. | Route[a] | Dose (mg/kg) | N size[b] | Formulation[d] | CMAX (ng/mL) | AUC (h·ng/mL) | CLT (mL/min/kg) | VSS (L/kg) | T-HALF (h) | F (%) |
|---|---|---|---|---|---|---|---|---|---|---|
| | | | | DOG | | | | | | |
| 9200008300 | IV | 0.5 | 2m | Propylene glycol:ethanol: phosphate buffer (40:5:55) | 540 | 167 | 25.7 | 4.7 | 3.9 | n.a. |
| | Oral | 1 | 3m | Propylene glycol:ethanol: phosphate buffer (40:5:55) | 263 | 273 | n.a. | n.a. | 3.1 | 40 |
| 9200009040 | IV | 0.055 | 2m, 2f[k] | 50 mM citrate buffer (pH 5) | 104 | 48.3 | n.d. | n.d. | n.d. | n.a. |
| | IV | 0.27 | 2m, 2f[k] | 50 mM citrate buffer (pH 5) | 664 | 362 | n.d. | n.d. | n.d. | n.a. | a    IA and IV represents intraarterial and intravenous route of administration, respectively.
b    m=males and f=females.
c    All formulations were solution formulations. Phosphate buffers, when used in the formulations, had pH 7.4-8.0.
d    represents 3 animals per time point for a composite profile; total number of animals per group were 15.
e    n.a. = not applicable.
f    AUC=TAUC(0-10); 10 h was the last plasma collection time.
g    n.d. = not determined.
h    %F determined with respect to propylene glycol:ethanol:water formulation.
i    AUC=TAUC(0-48); 48 h was the last plasma collection time.
j    %F determined with respect to ethanol:phosphate buffer formulation.
k    parameters were combined across gender due to limited sample size per gender.

ORAL ADMINISTRATION OF EPOTHILONES

CROSS-REFERENCE TO RELATED APPLICATION

This application claims priority from provisional application Ser. No. 60/370,104, filed Apr. 4, 2002, incorporated herein by reference in its entirety.

FIELD OF THE INVENTION

The invention relates to methods of orally administering epothilones to a patient in a manner that increases bioavailablity. The invention further relates to pharmaceutical compositions, pharmaceutical dosage forms, and kits for use in the methods of the invention. In particular, the invention relates to a solid oral dosage form of an epothilone.

BACKGROUND OF THE INVENTION

Epothilones are 16 member cyclic macrolide molecules which find utility in the pharmaceutical field. For example, Epothilone A and B are naturally occurring compounds that can be isolated from certain microorganisms; these two compounds have the following structures:

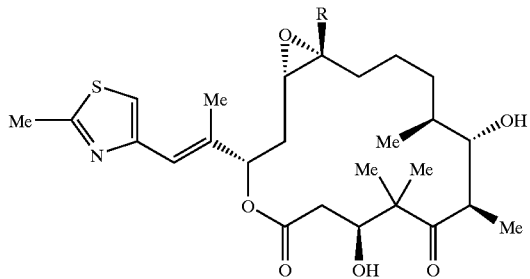

Epothilone A R=H
Epothilone B R=Me

Since the introduction of epothilones into the art, many groups have been designing, synthesizing and testing analogs of the naturally occurring epothilones in an attempt to develop useful pharmaceuticals. (See, e.g., D. Schinzer et al., *Angew. Chem. Int. Ed. Engl.*, 1997, 36, No. 3, 523–524; K. C. Nicolaou, et al., *J. Amer. Chem. Soc.*, 1997, 119, 7974–7991; K. C. Nicaloau et al., *Angew. Chem. Int. Ed. Engl.*, 1996, 35, No. 20, 2399–2401; A. Balog et al., *Angew. Chem. Int. Ed. Engl.*, 1996, 35, No. 23/24, 2801–2803).

Known epothilones exert microtubule-stabilizing effects similar to Taxol® and therefore exhibit cytotoxic activity against rapidly proliferating cells, such as occur in cancer and other hyperproliferative cellular diseases (See *Angew. Chem. Int. Ed. Engl.*, Vol. 35, No. 13/14, 1996 and D. M. Bollag, *Exp. Opin. Invest. Drugs*, 6(7): 867–873, 1997).

Before epothilones can be used to treat diseases in patients, however, they must be formulated into a pharmaceutical composition that can be administered to the patient; for example, into a dosage form suitable for oral, mucosal (e.g., nasal, sublingual, vaginal, buccal, or rectal), parenteral (e.g., subcutaneous, intravenous, bolus injection, intramuscular, or intraarterial), or transdermal administration. Formulations for oral administration are particularly preferred since they are more convenient and easier to administer than other formulations. Also, the oral route of administration avoids the pain and discomfort of parenteral administration. Accordingly, formulations for oral administration are preferred by patients and result in better patient compliance with dosing schedules.

The usefulness of an oral formulation, however, requires that the active agent be bioavailable. Bioavailability of orally administered drugs is affected by various factors including, for example, drug absorption throughout the gastrointestinal tract, stability of the drug in the gastrointestinal tract, and the first pass effect. Thus, effective oral delivery of an active agent requires that the active agent have sufficient stability in the stomach and intestinal lumen to pass through the intestinal wall. Many drugs, however, tend to degrade quickly in the intestinal tract or have poor absorption in the intestinal tract so that oral administration is not an effective method for administering the drug.

Pharmaceutical compositions intended for oral administration are typically solid dosage forms (e.g., tablets) or liquid preparations (e.g., solutions, suspensions, or elixirs). Solid dosage forms, however, can impose restrictions on the pharmaceutical use of the active agent since some patient populations have difficulty, either physical or psychological, in swallowing solid oral dosage forms. If a liquid dosage form is available, these patients could more easily take the required dose of active ingredient by having it administered in the form of an oral liquid preparation that they can drink or having it administered, for example, by a naso-gastric tube. Thus, liquid oral dosage forms are desirable.

Liquid oral pharmaceutical compositions require a suitable solvent or carrier system to dissolve or disperse the active agent to enable the composition to be administered to a patient. The solvent system must be compatible with the active agent and be non-toxic to the patient. Commonly, the solvent for liquid oral formulations is a water based solvent.

The formulation of certain epothilones presents difficulties in addition to the normal hurdles, in that certain epothilones are either or both acid labile and/or poorly soluble in aqueous media, which is the media of first choice for oral solutions. The present invention, however, overcomes these difficulties and provides methods and pharmaceutical formulations for the oral administration of epothilones wherein the epothilones are sufficiently bioavailable to have a pharmacological effect.

SUMMARY OF THE INVENTION

The present invention encompasses a method of orally delivering epothilones to a mammal while reducing or avoiding the degradation, decomposition, or deactivation of the epothilone by the gastrointestinal system, particularly by gastric fluid in the stomach. In one embodiment, the method encompasses administering the epothilone in, or with, a pharmaceutically acceptable acid neutralizing buffer. In a preferred embodiment, the administration comprises the use of two solutions, one comprising the active epothilone alone, or in a pharmaceutically acceptable carrier, and the other comprising the pharmaceutically acceptable neutralizing buffer.

The invention therefore includes pharmaceutical compositions comprising an epothilone either in a solid form which is suitable for constitution, or reconstitution if lyophilized, into a pharmaceutically acceptable solution or as a pre-made solution. The invention also encompasses aqueous pharmaceutical compositions. The invention further encompasses pharmaceutical compositions comprising a pharmaceutically acceptable neutralizing buffer either in solid form suitable for constitution, or reconstitution if lyophilized, into a pharmaceutically acceptable solution or as a pre-made solution.

In a more specific embodiment, the present invention is directed to methods of increasing the bioavailability of an orally administered epothilone. The methods involve orally administering one or more epothilones of Formula I:

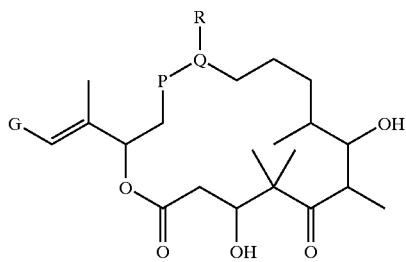

I wherein:
P-Q is a C, C double bond or an epoxide;
G is

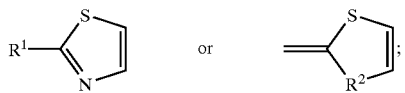

R is selected from the group of H, alkyl, and substituted alkyl;
R$^1$ is selected from the group consisting of

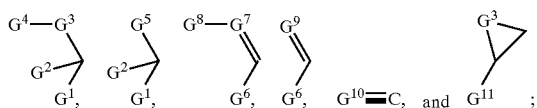

R$^2$ is

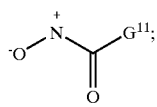

G$^1$ is selected from the group of H, halogen, CN, alkyl and substituted alkyl;
G$^2$ is selected from the group of H, alkyl, and substituted alkyl;
G$^3$ is selected from the group of O, S, and NZ$^1$;
G$^4$ is selected from the group of H, alkyl, substituted alkyl, OZ$^2$, NZ$^2$Z$^3$, Z$^2$C=O, Z$^4$SO$_2$, and optionally substituted glycosyl;
G$^5$ is selected from the group of halogen, N$_3$, NCS, SH, CN, NC, N(Z$^1$)$_3$$^+$ and heteroaryl;
G$^6$ is selected from the group of H, alkyl, substituted alkyl, CF$_3$, OZ$^5$, SZ$^5$, and NZ$^5$Z$^6$;
G$^7$ is CZ$^7$ or N;
G$^8$ is selected from the group of H, halogen, alkyl, substituted alkyl, OZ$^{10}$, SZ$^{10}$, NZ$^{10}$Z$^{11}$;
G$^9$ is selected from the group of O, S, —NH—NH— and —N=N—;
G$^{10}$ is N or CZ$^{12}$;
G$^{11}$ is selected from the group of H$_2$N, substituted H$_2$N, alkyl, substituted alkyl, aryl, and substituted aryl;
Z$^1$, Z$^6$, Z$^9$, and Z$^{11}$ are independently selected from the group H, alkyl, substituted alkyl, acyl, and substituted acyl;
Z$^2$ is selected from the group of H, alkyl, substituted alkyl, aryl, substituted aryl, and heterocycle;

Z$^3$, Z$^5$, Z$^8$, and Z$^{10}$ are independently selected from the group H, alkyl, substituted alkyl, acyl, substituted acyl, aryl, and substituted aryl;
Z$^4$ is selected from the group of alkyl, substituted alkyl, aryl, substituted aryl, and heterocycle;
Z$^7$ is selected from the group of H, halogen, alkyl, substituted alkyl, aryl, substituted aryl, OZ$^8$, SZ$^8$, and NZ$^8$Z$^9$; and
Z$^{12}$ is selected from the group of H, halogen, alkyl, substituted alkyl, aryl, and substituted aryl;
with the proviso that when R$^1$ is

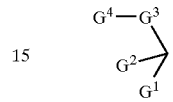

G$^1$, G$^2$, G$^3$ and G$^4$ cannot simultaneously have the following meanings:
G$^1$ and G$^2$=H, G$^3$=O and G$^4$=H or Z$^2$C=O where Z$^2$=alkyl group,
and with the proviso that when R$^1$ is

G$^1$, G$^2$ or G$^5$ cannot simultaneously have the following meanings: G$^1$ and G$^2$=H, and G$^5$=F;
or a pharmaceutically acceptable salt, solvate, hydrate, clathrate or prodrug thereof;
and optionally orally administering one or more pharmaceutically acceptable acid neutralizing buffers.

Formula Ia provides another example of an epothilone suitable for use in the methods, compositions and kits of the present invention:

Ia

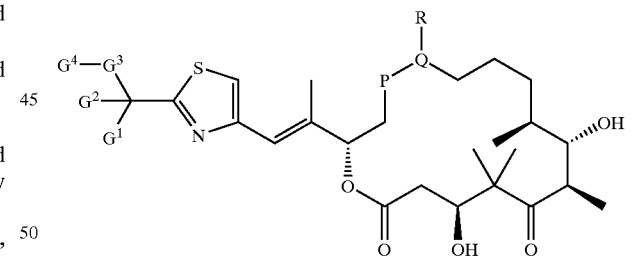

where the symbols have the following meaning:
P-Q is a C,C double bond or an epoxide,
R is a H atom or a methyl group,
G$^1$ is an H atom, an alkyl group, a substituted alkyl group or a halogen atom,
G$^2$ is an H atom, an alkyl group or a substituted alkyl group,
G$^3$ is an O atom, an S atom or an NZ$^1$ group with
Z$^1$ being an H atom, an alkyl group, a substituted alkyl group, an acyl group, or a substituted acyl group, and
G$^4$ is an H atom, an alkyl group, a substituted alkyl group, an OZ$^2$ group, an NZ$^2$Z$^3$ group, a Z$^2$C=O group, a Z$^4$SO$_2$ group or an optionally substituted glycosyl group with Z$^2$ being a H atom, an alkyl group, a substituted alkyl group, an aryl group, a substituted aryl group or a heterocyclic group, $Z^3$ an H atom, an alkyl group, a substituted alkyl group, an acyl group or a substituted acyl group, and $Z^4$ an alkyl, a substituted alkyl, an aryl, a substituted aryl or a heterocyclic group, with the proviso that $G^1$, $G^2$, $G^3$ and $G^4$ cannot have simultaneously the following meanings: $G^1$ and $G^2$=H atom, $G^3$=O atom and G=H atom or $Z^2C$=O with $Z^2$=alkyl group.

A preferred compound of formula Ia is the compound of formula Ib:

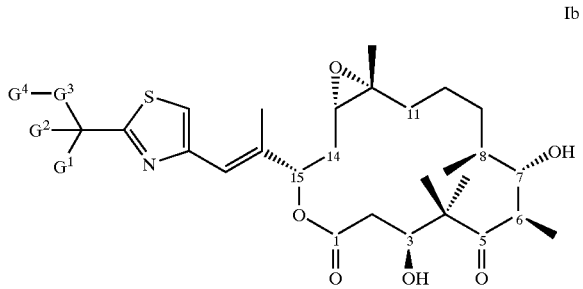

where $G^1$, $G^2$, $G^3$, $G^4$, $Z^1$, $Z^2$ and $Z^3$ are as defined above.

Formula Ic provides yet another example of an epothilone suitable for use in the methods, compositions and kits of the present invention:

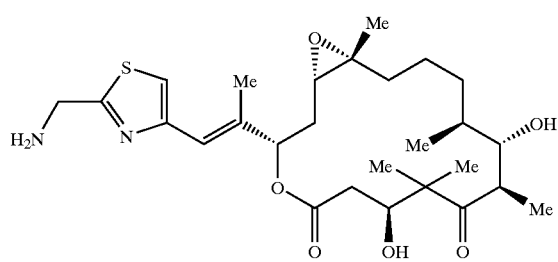

The pharmaceutically acceptable acid neutralizing buffer may be administered concurrently with, before, after, or both before and after administration of the one or more epothilones of interest. When administered before the active epothilone, the pharmaceutically acceptable acid neutralizing buffer is administered not more than about 1 hour before the epothilone is administered. When administered after, the pharmaceutically acceptable acid neutralizing buffer is administered not more than about 1 hour after the epothilone is administered.

The pharmaceutically acceptable acid neutralizing buffer solution, which may be a liquid formulation and which may be constituted immediately prior to administration, comprises one or more components that are capable of neutralizing acidic solutions, particularly gastric fluid, for a period of time. The buffer components include, but are not limited to, pharmaceutically acceptable weak acids, weak bases, or mixtures thereof. Preferably, the buffer components are water soluble materials such as phosphoric acid, tartaric acids, lactic acid, succinic acid, citric acid, acetic acid, ascorbic acid, aspartic acid, hydrochloric acid, sulfuric acid, glutamic acid, and salts thereof.

The pharmaceutically acceptable acid neutralizing buffer is administered in an amount sufficient to neutralize gastric fluids in the stomach and increase the amount of the epothilone that is absorbed by the gastrointestinal system. The pharmaceutically acceptable acid neutralizing buffer may be administered as an aqueous solution having a pH of between about 5 to 9. The pharmaceutically acceptable acid neutralizing buffer may be administered as an aqueous solution of anhydrous dibasic sodium phosphate, sodium citrate dihydrate, and anhydrous citric acid.

The present invention increases the bioavailability of the orally administered epothilone significantly above that of an epothilone orally administered without a neutralizing buffer. In one embodiment the bioavailability of the one or more epothilones or a pharmaceutically acceptable salt, solvate, clathrate, hydrate, or prodrug thereof is at least 20 percent. The one or more epothilones or a pharmaceutically acceptable salt, solvate, clathrate, hydrate, or prodrug thereof may be orally administered as a solution in propylene glycol and ethanol, for example, wherein the ratio of propylene glycol:ethanol is about 80:20.

A preferred epothilone is [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (epothilone of formula Ic, Compound A).

The invention also encompasses kits which comprise the desired epothilone and a soluble buffer composition. The invention encompasses a kit comprising (a) a pharmaceutical composition comprising an epothilone which is suitable for oral administration and (b) a pharmaceutical composition comprising an acid neutralizing buffer which is suitable for oral administration.

In one embodiment the kits include:

(i) a first component comprising one or more epothilones of Formula I, Ia, Ib or Ic:

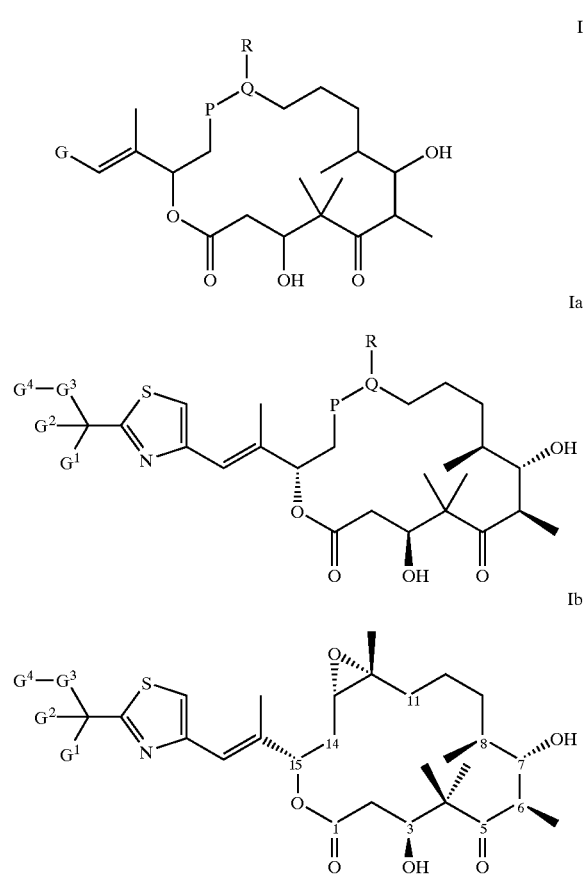

-continued

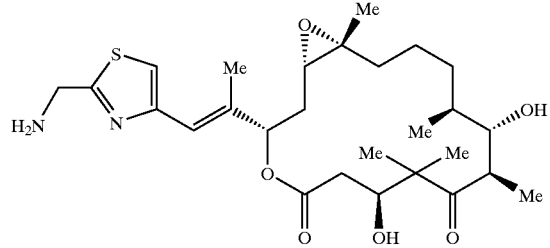

Ic wherein G, $G^1$, $G^2$, $G^3$, $G^4$, $G^5$, $G^6$, $G^7$, $G^8$, $G^9$, $G^{10}$, $G^{11}$, P, Q, R, $R^1$, $R^2$, Z, $Z^1$, $Z^2$, $Z^3$, $Z^4$, $Z^5$, $Z^6$, $Z^7$, $Z^8$, $Z^9$, and $Z^{10}$ are defined above; and (ii) a second component comprising a pharmaceutically acceptable acid neutralizing buffer, wherein the first component and the second component are provided as a liquid oral dosage form or as a solid pharmaceutical composition that can be constituted or reconstituted with a solvent to provide a liquid oral dosage.

The pharmaceutical composition to be reconstituted with a solvent may be provided as a tablet. The first component or the second component may be anhydrous. The kit may optionally include solvents for reconstituting the first or second components. The solvent for reconstituting the first component may be a mixture of propylene glycol and ethanol, wherein the ratio of propylene glycol:ethanol is about 80:20.

The invention is further directed to a pharmaceutical composition comprising:

(i) one or more epothilones of Formula I, Ia, Ib or Ic:

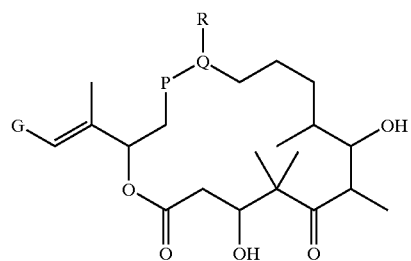

I

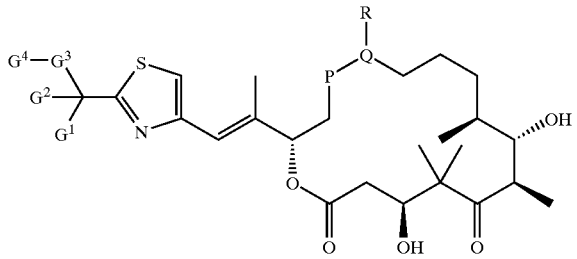

Ia

-continued

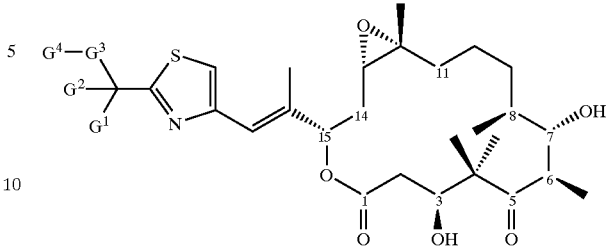

Ib

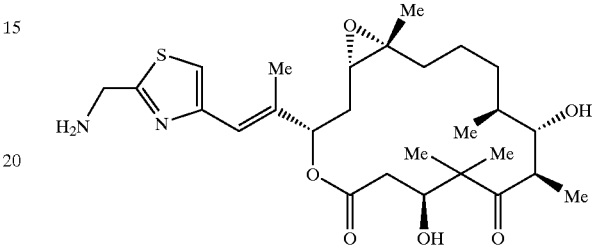

Ic wherein G, $G^1$, $G^2$, $G^3$, $G^4$, $G^5$, $G^6$, $G^7$, $G^8$, $G^9$, $G^{10}$, $G^{11}$, P, Q, R, $R^1$, $R^2$, Z, $Z^1$, $Z^2$, $Z^3$, $Z^4$, $Z^5$, $Z^6$, $Z^7$, $Z^8$, $Z^9$ and $Z^{10}$ are defined above; or a pharmaceutically acceptable salt, solvate, clathrate, hydrate or prodrug thereof in solid form; and (ii) a solid pharmaceutically acceptable acid neutralizing buffer in an amount sufficient to reduce decomposition of the one or more epothilones, or a pharmaceutically acceptable salt, solvate, clathrate, hydrate, or prodrug thereof when the pharmaceutical composition is reconstituted with a solvent to provide a liquid oral dosage form.

BRIEF DESCRIPTION OF THE DRAWINGS

FIG. 2: FIG. 2(A) shows the comparitive antitumor activity of IV epothilones of formula Ic and Id in the Pat-7 human ovarian carcinoma model. The compounds were administered at the indicated doses, every 4 days for a total of 3 administrations starting 10 days after tumor implantation Q4D×3;10). Each datum point represents the median tumor weight of 8 mice. FIG. 2(B) shows the dose-response relationship for the epothilone of formula Ic in the Pat-7 tumor model.

FIG. 5(A) shows effects of various infusional doses of epothilone of formula Ic on sc Pat-7 tumor growth.

The epothilone of formula Ic was administered by infusion over a 10-hr period, 5% of the dose was given as loading dose. FIG. 5(B) shows plasma concentrations of the epothilone of formula Ic following infusional treatment with this epothilone at various doses. Error bars represent 1 S.D.

FIG. 6: FIGS. 6(A) and 6(B) show the mean pharmacokinetic parameters of Compound A in preclinical studies.

DETAILED DESCRIPTION OF THE INVENTION

Figure 1:
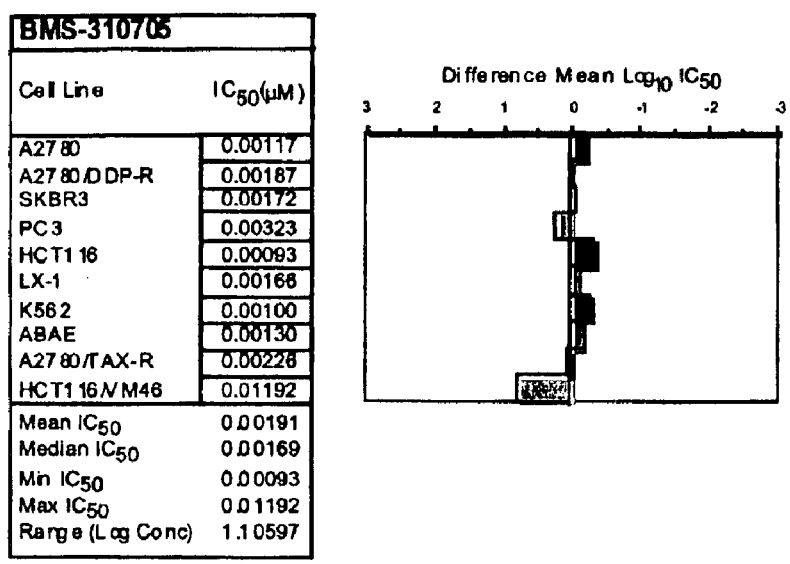
FIG. 1 shows the cytotoxicity spectrum of epothilone of formula Ic in a panel of eight tumor cell lines. The bar graph (on the right) depicts the $IC_{50}$ values of the cell lines listed on the left (top to bottom).

Based upon the pharmacological benefits of epothilones, there is need for dosage forms and methods for administering these compounds so that they are sufficiently bioavailable to have a pharmacological effect. In particular, there is a need for oral dosage forms and more particularly for liquid oral dosage forms that can deliver an amount of epothilone sufficient to treat disease. The present invention is based, in part, on the discovery that epothilones of Formula I, Ia, Ib or Ic:

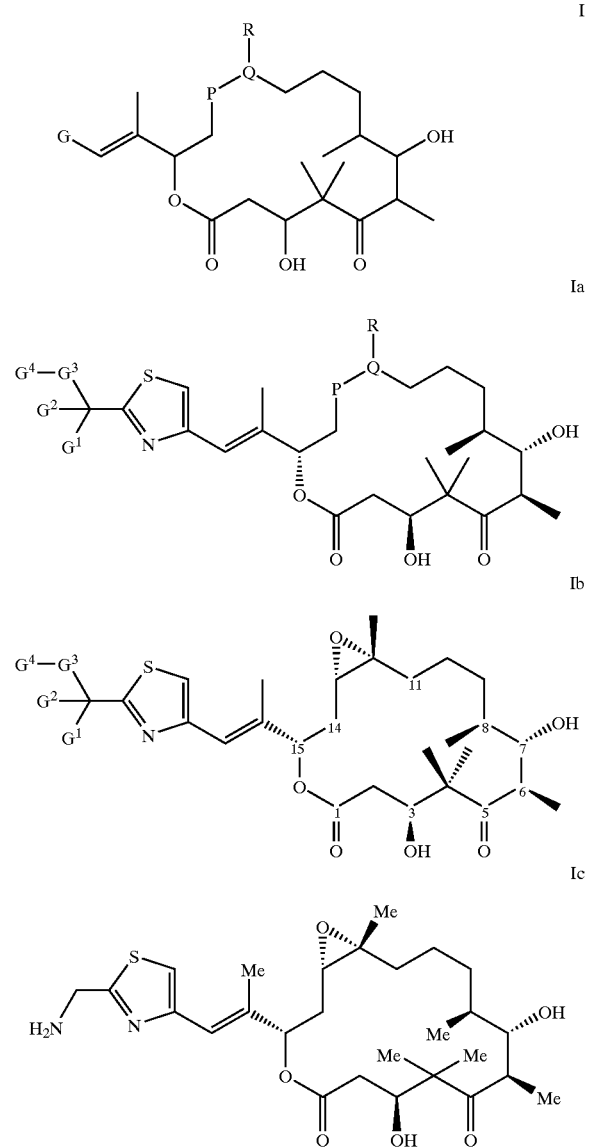

wherein G, $G^1$, $G^2$, $G^3$, $G^4$, $G^5$, $G^6$, $G^7$, $G^8$, $G^9$, $G^{10}$, $G^{11}$, P, Q, R, $R^1$, $R^2$, Z, $Z^1$, $Z^2$, $Z^3$, $Z^4$, $Z^5$, $Z^6$, $Z^7$, $Z^8$, $Z^9$ and $Z^{10}$ are as defined above;

and pharmaceutically acceptable salts, solvates, hydrates, clathrates or prodrugs thereof, when orally administered in combination with a pharmaceutically acceptable acid neutralizing buffer, are sufficiently bioavailable to have a pharmacological effect. Accordingly, the invention is directed to methods of increasing the bioavailability of orally administered epothilones of Formula I, Ia, Ib or Ic, or a pharmaceutically acceptable salt, solvate, clathrate, hydrate, or prodrug thereof, by orally administering the one or more epothilones of Formula I, Ia, Ib or Ic, or a pharmaceutically acceptable salt, solvate, clathrate, hydrate, or prodrug thereof, and orally administering a pharmaceutically acceptable acid neutralizing buffer in combination therewith. The invention also relates to pharmaceutical compositions, pharmaceutical dosage forms, and kits for use in the methods of the invention.

A preferred epothilone for use in the methods, compositions, and dosage forms of the invention is [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (epothilone of formula Ic, Compound A, BMS-310705), depicted below:

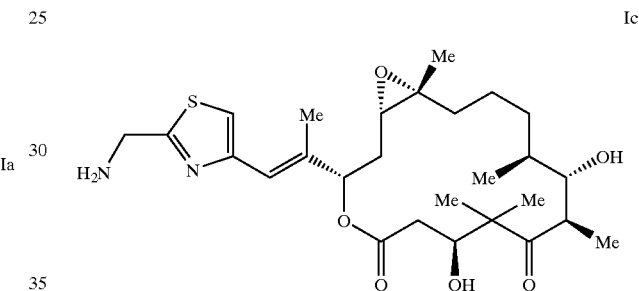

Definitions

Listed below are definitions of various terms used to describe this invention. These definitions apply to the terms as they are used throughout this specification, unless otherwise indicated in specific instances.

As used herein, the term "alkyl" refers to straight or branched chain unsubstituted hydrocarbon groups of 1 to 20 carbon atoms, preferably 1 to 7 carbon atoms.

As used herein, the term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, and pyrimidyl. Where noted above where the substituent is further substituted it will be with halogen, alkyl, alkoxy, aryl or aralkyl.

As used herein, the term "halogen" or "halo" refers to fluorine, chlorine, bromine and iodine.

As used herein, the term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

As used herein, the term "aralkyl" refers to an aryl group bonded directly through an alkyl group, such as benzyl.

As used herein, the term "substituted aryl" refers to an aryl group substituted by, for example, one to four substituents such as alkyl; substituted alkyl, phenyl, substituted phenyl, heterocyclo, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkylsulfonyl, sulfonamido, and aryloxy. The substituent may be further substituted by halo, hydroxy, alkyl, alkoxy, aryl, substituted aryl, substituted alkyl or aralkyl.

As used herein, the term "cycloalkyl" refers to optionally substituted, saturated cyclic hydrocarbon ring systems, preferably containing 1 to 3 rings and 3 to 7 carbons per ring which may be further fused with an unsaturated C3–C7 carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the terms "heterocycle", "heterocyclic" and "heterocyclo" refer to an optionally substituted, fully saturated or unsaturated, aromatic or nonaromatic cyclic group, for example, a 4 to 15 membered system or a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include, but are not limited to, pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl.

Exemplary bicyclic heterocyclic groups include, but are not limited to, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo [3,1-b]pyridinyl or furo [2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl.

Exemplary substituents include, but are not limited to, one or more alkyl groups as described above or one or more groups described above as alkyl substituents. Also included are smaller heterocyclos, such as, epoxides and aziridines.

As used herein, the term "heteroatoms" shall include oxygen, sulfur and nitrogen.

As used herein, the prefix "lower" stands for a moiety having up to and including 7, preferably up to and including 4 carbon atoms.

As used herein, the term "bioavailable" means the extent to which a drug is absorbed into a living system and made available in the circulating blood of the living system. Methods to determine the bioavailability of drugs are well known to those of ordinary skill in the art.

As used herein, the phrase "sufficiently bioavailable to have a pharmacological effect" means that the epothilones are greater than 20 percent bioavailable, preferably greater than 30 percent bioavailable, and more preferably greater than 50 percent bioavailable.

As used herein, the term "pharmaceutically acceptable salt" refers to a salt prepared from an epothilone of Formula I, Ia, Ib or Ic having a basic functional group, such as an amine, with a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. Salts formed with acids can be obtained, for example, with an epothilone of Formula I, Ia, Ib or Ic having a basic functional group and an equivalent amount of a non-toxic acid to provide an acid addition salt. The reaction is typically carried out in a medium in which the acid addition salt precipitates or an aqueous medium followed by evaporation. The term "pharmaceutically acceptable salt" also refers to a salt prepared from an epothilone of Formula I, Ia, Ib or Ic having an acidic functional group, such as a carboxylic acid functional group, and a pharmaceutically acceptable non-toxic inorganic or organic base. Suitable non-toxic bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2- hydroxyethyl)amine, or tri-(2-hydroxyethyl)amine; N-methyl-D-glucamine; and amino acids such as arginine, lysine, and the like. Salts formed with bases can be obtained, for example, with an epothilone of Formula I, Ia, Ib or Ic having an acidic functional group and an equivalent amount of a non-toxic base. The reaction is typically carried out in a medium in which the salt precipitates or an aqueous medium followed by evaporation.

The invention also includes zwitterions.

As used herein, the term "pharmaceutically acceptable acid neutralizing buffer" refers to a combination of a pharmaceutically acceptable non-toxic acid and a pharmaceutically acceptable non-toxic salt of an acid that when added to a solution provides a solution that is more resistant to change of pH, compared to a solution without the buffer, when acid or alkali is added to the solution. The term "pharmaceutically acceptable acid neutralizing buffer" also includes compounds, such as basic compounds, that when added to an acidic solution neutralizes the acid and increases the pH of the solution.

As used herein, the term "clathrate" means an inclusion compound formed by the envelopment of a molecule of a "guest" compound in a cage-like hollow space formed by combination of several molecules of a "host" compound.

As used herein, the term "pro-drug" means a derivative of a compound that can hydrolyze, oxidize, or otherwise react under biological conditions (in vitro or in vivo) to provide an epothilone compound of Formula I, Ia, Ib or Ic. For example, carboxylic esters are conveniently formed by esterifying carboxylic acid functionalities; if the epothilone of Formula I, Ia, Ib or Ic includes an acid functional group it can be esterified to provide a pro-drug. Various pro-drugs are well known in the art (For examples of pro-drugs, see: Design of Prodrugs, edited by H. Bundgaard, Elsevier, 1985; Methods in Enzymology, vol. 42, p. 309–396, edited by K. Widder et al., Academic Press, 1985; A Textbook of Drug Design and Development, edited by Krosgaard-Larsen and H, Bundgaard, chapter 5, "Design and Application of Prodrugs," by H. Bundgaard, p. 113–191, 1991; H. Bundgaard, Advanced Drug Delivery Reviews," 8, 1–38, 1992; H. Bundgaard et al., Journal of Pharmaceutical Sciences, 77, 285, 1988; and N. Kakeya et al., Chem. Phar. Bull., 32, 692, 1984).

As used herein, the phrase "acid neutralization capacity," means the quantity of 1N HCl (expressed in milliequivalents) that can be brought to pH 3.5, as defined in the U.S. Pharmacopeia, 301.

As used herein, the term "solution" means a liquid preparation that contains one or more soluble active ingredients dissolved in a solvent.

As used herein, the term "suspension" means a finely divided, undissolved active ingredient suspended in a solvent.

As used herein, the term "elixir" means a solution of an active ingredient in a solvent containing water and alcohol.

As used herein, the term "syrup" means a concentrated solution of sugar, such as sucrose, in water or other aqueous liquid, optionally containing polyols, such as glycerin or sorbitol to retard crystallization of the sugar or increase solubility of the added ingredients.

Epothilones Useful in the Methods, Compositions, and Dosage Forms of the Invention Any epothilone can be used in the methods, compositions, and dosage forms of the invention. Preferably, the epothilones are acid labile and poorly soluble in water such that they are not readily bioavailable by the oral route. In a specific embodiment the epothilones of Formula I, Ia, Ib or Ic are used in the methods, compositions, and dosage forms of the invention. Epothilones of Formula I can be prepared by the methods disclosed in U.S. Pat. No. 6,262,094, issued Jul. 17, 2001, the contents of which are expressly incorporated herein. One of ordinary skill in the art would also recognize that the epothilones of Formula I, Ia, Ib or Ic could also be prepared by suitable modification of the methodologies disclosed in, for example, K. C. Nicolau et al., "An Approach to Epothilones Based on Olefin Metathesis," Angew. Chem Int. Ed. Engl., 35(20): 2399–2401 (1996); K. C. Nicolau et al., "The Total Synthesis of Epothilone A: The Macrolactonization Approach," Angew. Chem Int. Ed. Engl., 36(5): 525–527 (1997); K. C. Nicolau et al., "Designed Epothilones: Combinatorial Synthesis, Tubulin Assembly Properties, and Cytoxic Action Against Taxol Resistant Tumor Cells," Angew. Chem Int. Ed. Engl., 36(19): 2097–2103 (1997); K. C. Nicolaou et al., "The Olefin Metathesis Approach to Epothilone A and its Analogues", J. Am. Chem. Soc., 119(34): 7960–7973 (1997); K. C. Nicolaou et al., "Total Syntheses of Epothilones A and B via a Macrolactonization-Based Strategy," J. Am. Chem. Soc., 119(34): 7974–7991 (1997); K. C. Nicolaou et al., "Synthesis of Epothilones A and B in Solid and Solution Phase," Nature, 387: 268–272 (1997); and D. Meng et al., "Remote Effects in Macrolide Formation Through Ring-Forming Olefin Metathesis: An Application to the Synthesis of Fully Active Epothilone Congeners," J. Am. Chem. Soc., Vol. 119, No. 11, 2733–2734 (1997).

Preferably, the epothilones are crystalline and anhydrous. Optionally, the epothilones are sterilized before being used in the compositions of the invention.

Utility and Uses of the Epothilones or Compositions Thereof

The epothilones of the invention are microtubule-stabilizing agents and, thus, can be used to treat a variety of cancer or other diseases of abnormal cell proliferation. The methods of the invention are particularly useful for administering one or more epothilones of Formula I, Ia, Ib or Ic, or a pharmaceutically acceptable salt, solvate, clathrate, hydrate, or prodrug thereof, to a patient suffering from cancer or other hyperproliferative cellular disease. As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the methods of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma.

The methods of the invention are useful for treating patients who have been previously treated for cancer, as well as those who have not previously been treated for cancer. Indeed, the methods and compositions of this invention can be used in first-line and second-line cancer treatments.

The methods of the invention are also useful in combination with known anti-cancer treatments, including radiation. The methods of the invention are especially useful in combination with anti-cancer treatments that involve administering a second drug that acts in a different phase of the cell cycle, e.g., S phase, than the epothilones of Formula I, Ia, Ib or Ic, which exert their effects at the $G_2$-M phase.

Epothilones of Formula I, Ia, Ib or Ic may also inhibit tumor angiogenesis, thereby affecting abnormal cellular proliferation. Accordingly, the methods of the invention may also be useful in treating certain forms of blindness related to retinal vascularization, arthritis, especially inflammatory arthritis, multiple sclerosis, restinosis, and psoriasis.

Epothilones of Formula I, Ia, Ib or Ic may also induce or inhibit apoptosis, a physiological cell death process critical for normal development and homeostasis. Alterations of apoptotic pathways contribute to the pathogenesis of a variety of human diseases. Accordingly, the methods of the invention will be useful in the treatment of a variety of human diseases with aberrations in apoptosis including cancer (particularly, but not limited to, follicular lymphomas, carcinomas with p53 mutations, hormone dependent tumors of the breast, prostrate and ovary, and precancerous lesions such as familial adenomatous polyposis), viral infections (including, but not limited to, herpesvirus, poxyvirus, Epstein-Barr virus, Sindbis virus and adenovirus), autoimmune diseases (including, but not limited to, systemic lupus erythematosus, immune mediated glomerulonephritis, rheumatoid arthritis, psoriasis, inflammatory bowel diseases and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

Epothilones of Formula I, Ia, Ib or Ic may also be formulated or co-administered with other therapeutic agents that are selected for their particular usefulness in administering therapies associates with the aforementioned conditions. For example, each of the compounds of formula I, Ia, Ib or Ic may be formulated with agents to prevent nausea, hypersensitivity, and gastric irritation, such as anti-emetics, and $H_1$ and $H_2$ antihistamines. The above therapeutic agents, when employed in combination with the epothilones of Formula I, Ia, Ib or Ic, may be used in those amounts indicated in the Physicians' Desk Reference (PDR) or as otherwise determined by one of ordinary skill in the art.

Buffers Useful in the Methods, Compositions, and Dosage Forms of the Invention

The purpose of the buffer in the methods of the invention is to temporarily neutralize gastric fluid and thereby reduce degradation of the epothilone in the stomach of the patient. In addition, in aqueous and partially aqueous liquid oral formulations comprising one or more epothilones of Formula I, Ia, Ib or Ic, or a pharmaceutically acceptable salt, solvate, clathrate, hydrate, or prodrug thereof, the buffer reduces decomposition of the epothilone of Formula I, Ia, Ib or Ic. Applicants have surprisingly discovered that liquid oral dosage forms comprising one or more epothilones of Formula I, Ia, Ib or Ic, or a pharmaceutically acceptable salt, solvate, clathrate, hydrate, or prodrug thereof, and a buffer are more stable than a liquid oral dosage form without a buffer.

Buffers useful in the methods, compositions, and dosage forms of the invention may be readily prepared by combining one or more acids and the salt of one or more acids in a ratio such that the combination, when dissolved in an aqueous solution, provides a solution having a pH of between about 5 and 9. Typically, the one or more acids will have a pKa of between about 4 and 10. One of ordinary skill in the art would readily recognize how to prepare buffers that provide a solution having the desired pH value. In addition, the invention contemplates for use as a buffer compounds, such as basic compounds, that when added to an acidic solution increase the pH of the solution.

Those skilled in the art would readily recognize a variety of buffers that could be used in the methods, compositions, and dosage forms of the invention. Typical buffers include, but are not limited to pharmaceutically acceptable weak acids, weak bases, or mixtures thereof. Preferably, the buffer components are water soluble materials such as phosphoric acid, tartaric acids, lactic acid, succinic acid, citric acid, acetic acid, ascorbic acid, aspartic acid, glutamic acid, and salts thereof. Preferably, the pharmaceutically acceptable acid neutralizing buffer is a dibasic phosphate-monobasic phosphate buffer or a dibasic phosphate buffer-citric acid-citrate buffer. These buffers are commercially available or can be readily prepared by one of ordinary skill in the art using commercially available buffering agents such as those mentioned above.

Methods of Orally Administering Acid Labile Epothilones of Formula I, Ia, Ib or Ic The invention encompasses methods of increasing the bioavailability of orally administered epothilones by orally administering an epothilone of Formula I, Ia, Ib or Ic, or a pharmaceutically acceptable salt, solvate, clathrate, hydrate, or prodrug thereof, and orally administering a pharmaceutically acceptable acid neutralizing buffer. The invention is particularly well suited for epothilones that are acid labile but may also be used with epothilones that are sensitive to hydrolysis under alkaline conditions and for epothilones that are not sensitive to hydrolyis. Further, the invention may be used with epothilones that are poorly soluble in aqueous media.

It should be recognized that the epothilones of the invention can be administered parenterally which would avoid the gastrointestinal system and overcome any bioavailability concerns. However, such administration is inconvenient and uncomfortable for the patient and provides other potential adverse effects. The compositions of this invention and the methods enable the oral route of administration to be used which is a significant advantage, particularly for human patients.

Administering one or more epothilones of Formula I, Ia, Ib or Ic, or a pharmaceutically acceptable salt, solvate, clathrate, hydrate, or prodrug thereof, in combination with a pharmaceutically acceptable acid neutralizing buffer provides increased bioavailability of the one or more epothilones of Formula I, Ia, Ib or Ic. Without being limited by theory, it is believed that the increased bioavailability is due, at least in significant part, to the buffer decreasing the rate of decomposition of the epothilones of Formula I, Ia, Ib or Ic, or a pharmaceutically acceptable salt, solvate, clathrate, hydrate, or prodrug thereof, in the acidic environment of the stomach. Certain epothilones, including the preferred epothilone of formula Ic, are unstable in acidic aqueous environments and decompose, presumably by an acid catalyzed hydrolytic opening of the epoxide ring. For example, the time for 5% drug loss ($t_{95}$) at 37° C. for an aqueous solution of Compound A is approximately 14 h at pH 7, but <0.2 hours at pH 2.5.

Thus, when epothilones of Formula I, Ia, Ib or Ic, or a pharmaceutically acceptable salt, solvate, clathrate, hydrate, or prodrug thereof, are orally administered they decompose in the stomach of the patient such that they are either minimally absorbed or not absorbed by the gastrointestinal tract.

When one or more epothilones of Formula I, Ia, Ib or Ic, or a pharmaceutically acceptable salt, solvate, clathrate, hydrate, or prodrug thereof, are administered to a patient in combination with a pharmaceutically acceptable acid neutralizing buffer, however, the buffer neutralizes acid in the stomach of the patient so that the rate of decomposition of the one or more epothilones of Formula I, Ia, Ib or Ic, or a pharmaceutically acceptable salt, solvate, clathrate, hydrate, or prodrug thereof is sufficiently decreased so that the one or more epothilones of Formula I, Ia, Ib or Ic, or a pharmaceutically acceptable salt, solvate, clathrate, hydrate, or prodrug thereof remain in the gastrointestinal tract for sufficient time to be absorbed.

In another embodiment of the invention an anti-acid such as hydroxides of aluminum and magnesium; carbonates, such as sodium carbonate and calcium carbonate; silicates; and phosphates can be used to neutralize the acid in the stomach before during or after epothilone administration.

When orally administered according to the methods of the invention, the epothilones of Formula I, Ia, Ib or Ic, or a pharmaceutically acceptable salt, solvate, clathrate, hydrate, or prodrug thereof are at least about 20% bioavailable, preferably at least about 40% bioavailable, and more preferably at least about 50% bioavailable.

In one embodiment of the invention, the one or more epothilones of Formula I, Ia, Ib or Ic, or a pharmaceutically acceptable salt, solvate, clathrate, hydrate, or prodrug thereof and the pharmaceutically acceptable acid neutralizing buffer are provided in a single oral dosage form and are administered simultaneously. The single composition comprising the combination of one or more epothilones of Formula I, Ia, Ib or Ic, or a pharmaceutically acceptable salt, solvate, clathrate, hydrate, or prodrug thereof, and the pharmaceutically acceptable acid neutralizing buffer may be administered as a solid oral dosage form (e.g., a tablet, capsule, or powder) or a liquid oral dosage form (e.g., a solution, suspension, or elixir). The solution or suspension can be constituted just prior to administration using the appropriate solvents or cosolvents to dissolve the epothilone and the buffer components.

For example, the one or more epothilones of Formula I, Ia, Ib or Ic, or a pharmaceutically acceptable salt, solvate, clathrate, hydrate, or prodrug thereof, and the pharmaceutically acceptable acid neutralizing buffer may be administered simultaneously as a solution of the epothilone of Formula I, Ia, Ib or Ic dissolved in a liquid comprising propylene glycol:ethanol:phosphate buffer (for example at IM, about pH 8) in a ratio of about 58:12:30, respectively.

In another embodiment of the invention, the epothilone of Formula I, Ia, Ib or Ic and the pharmaceutically acceptable acid neutralizing buffer are provided as separate distinct pharmaceutical compositions and are administered separately. Each of which are administered as a solid oral dosage form or a liquid oral dosage form.

When the one or more epothilones of Formula I, Ia, Ib or Ic, or a pharmaceutically acceptable salt, solvate, clathrate, hydrate, or prodrug thereof and the pharmaceutically acceptable acid neutralizing buffer are administered separately, the pharmaceutically acceptable acid neutralizing buffer may be orally administered before, after, or both before and after the desired epothilone of Formula I, Ia, Ib or Ic is administered. Preferably, the pharmaceutically acceptable acid neutralizing buffer is administered both before and after oral administration of the desired epothilone of Formula I, Ia, Ib or Ic, in an amount sufficient to neutralize the stomach acid. When the pharmaceutically acceptable acid neutralizing buffer is administered before the one or more epothilones of Formula I, Ia, Ib or Ic, or a pharmaceutically acceptable salt, solvate, clathrate, hydrate, or prodrug thereof, it is administered within about 5 hours, preferably within about 3 hours, more preferably within about 1 hour, and most preferably within about 10 minutes before the desired epothilone of Formula I, Ia, Ib or Ic is administered. When the pharmaceutically acceptable acid neutralizing buffer is administered after the desired epothilone of Formula I, Ia, Ib or Ic, or a pharmaceutically acceptable salt, solvate, clathrate, hydrate, or prodrug thereof, it is administered within about 5 hours, preferably within about 3 hours, more preferably within about 1 hour, and most preferably within about 10 minutes before the desired epothilone of Formula I, Ia, Ib or Ic is administered.

In another embodiment the epothilones of Formula I, Ia, Ib or Ic, or a pharmaceutically acceptable salt, solvate, clathrate, hydrate, or prodrug thereof, are administered as an enteric coated pill or capsule to delay release of the epothilone until after the pharmaceutically effective acid neutralizing buffer is administered. Enteric coated tablets and capsules are capsules coated with a substances that resist solution in a gastric fluid but disintegrate in the intestine.

In one embodiment the buffer is administered as a dispersible tablet.

The magnitude of the therapeutic dose of the desired epothilone of Formula I, Ia, Ib or Ic, or a pharmaceutically acceptable salt, solvate, clathrate, hydrate, or prodrug thereof, will typically vary with the specific disease and severity of the disease being treated. The dose, and perhaps the dose frequency, may also vary according to age, body weight, response, and the past medical history of the patient. Suitable dosing regimens can be readily selected by those skilled in the art with due consideration of such factors. Typically, the epothilone of Formula I, Ia, Ib or Ic, or a pharmaceutically acceptable salt, solvate, clathrate, hydrate, or prodrug thereof, is orally administered in a total amount of about 0.05 to about 200 mg/kg/day, preferably from about 5 to about 100 mg/kg/day, and more preferably less than about 100 mg/kg/day in a single dose or in about 2 to 4 divided doses.

The invention encompasses pharmaceutical unit dosage forms of the desired epothilone comprising 5 mg/unit, 10 mg/unit, 15 mg/unit, 20 mg/unit, 25 mg/unit, 50 mg/unit, and 100 mg/unit. Similarly, liquid unit doses encompassed by the invention include, but are not limited to, 2.5 mg/mL and 10 mg/mL.

The term "total amount," as used herein, means the combined amount of the epothilones of Formula I, Ia, Ib or Ic, or a pharmaceutically acceptable salt, solvate, clathrate, hydrate, or prodrug thereof, if more than one epothilone of Formula I, Ia, Ib or Ic, or a pharmaceutically acceptable salt, solvate, clathrate, hydrate, or prodrug thereof is in a unit dosage form or administered to the patient.

Further, the pharmaceutically acceptable acid neutralizing buffer is administered in an amount sufficient to deliver at least about 20 milliequivalents of acid neutralization capacity, preferably at least about 30 milliequivalents of acid neutralization capacity, more preferably at least about 40 milliequivalents of acid neutralization capacity, and most preferably at least about 50 milliequivalents of acid neutralization capacity.

The invention also encompasses pharmaceutical unit dosage forms of the desired buffer comprising about 5 to 100 mg/unit, preferably about 22.5 mg/unit, and more preferably about 22.5 mg/unit. Similarly, liquid unit doses of the buffer encompassed by the invention include about 5 to 100 mg/unit, preferably about 22.5 mg/unit, and more preferably about 22.5 mg/unit dissolved in about 50 to 300 mL of a solvent, preferably about 100 to 200 mL of a solvent, and more preferably about 150 mL of a solvent.

Typically, the pharmaceutically acceptable acid neutralizing buffer is administered as an aqueous solution having a pH of between about 5 to 9, preferably about 6 to 8.5, and more preferably about 7 to 8. Any pharmaceutically acceptable acid neutralizing buffer that provides a solution having a pH in the desired range may be used in the methods of the invention. Preferably, the pharmaceutically acceptable acid neutralizing buffer is a dibasic phosphate-monobasic phosphate buffer or a dibasic phosphate buffer-citric acid-citrate buffer.

In one embodiment of the invention, the patient is first administered the pharmaceutically acceptable acid neutralizing buffer as about 150 mL of an aqueous solution comprising anhydrous dibasic sodium phosphate (about 0.2 M), sodium citrate dihydrate (about 0.07 M), and anhydrous citric acid (about 0.008 M) at a pH of about 7.4; followed by oral administration of one or more epothilones of Formula I, Ia, Ib or Ic, or a pharmaceutically acceptable salt, solvate, clathrate, hydrate, or prodrug thereof as a liquid dosage form in a propylene glycol:ethanol system having a ratio of about 80:20; followed by oral administration of another about 150 mL aqueous solution comprising anhydrous dibasic sodium phosphate (about 0.2 M), sodium citrate dihydrate (about 0.07 M), and anhydrous citric acid (about 0.008 M) at a pH of about 7.4.

The methods of the present invention using epothilones of Formula I, Ia, Ib or Ic encompass dosing protocols such as once a day for 1 to 7 days, preferably for 3 to 7 days, every 1 to 10 weeks, preferably every 1 to 5 weeks, with a period of 1 to 3 weeks, preferably with a period of 1 week, where there is no treatment. In a preferred embodiment, an epothilone of Formula I, Ia, Ib or Ic is administered once a week every 3 weeks such that the treatment cycle comprises administration of the epothilone once a week followed by a period of 3 weeks when there is no treatment.

The methods of the present invention using epothilones of Formula I, Ia, Ib or Ic also encompass dosing protocols such as once a day for 2 to 10 days, preferably for 3 to 9 days, more preferably for 4 to 8 days and most preferably for 5 days. In one embodiment there is a period of 3 days to 5 weeks, preferably 4 days to 4 weeks, more preferably 5 days to 3 weeks, and most preferably 1 week to 2 weeks, in between cycles where there is no treatment. In another embodiment the epothilones of Formula I, Ia, Ib or Ic can be administered orally once a day for 3 days, with a period of preferably 1 week to 3 weeks in between cycles where there is no treatment. In yet another embodiment the epothilones of Formula I, Ia, Ib or Ic can be administered orally once a day for 5 days, with a period of preferably 1 week to 3 weeks in between cycles where there is no treatment.

In one preferred embodiment the treatment cycle for administration of the epothilones of Formula I, Ia, Ib or Ic is once daily for 3 consecutive days and the period between treatment cycles is from 2 days to 3 weeks, preferably one week.

In another preferred embodiment the treatment cycle for administration of the epothilones of Formula I, Ia, Ib or Ic is once daily for 5 consecutive days and the period between treatment cycles is from 2 days to 3 weeks, preferably one week.

In yet another preferred embodiment the treatment cycle for administration of the epothilones of Formula I, Ia, Ib or Ic is once daily for 7 consecutive days and the period between treatment cycles is from 2 days to 3 weeks, preferably one week.

The epothilones of Formula I, Ia, Ib or Ic can also be administered orally once every 1 to 10 weeks, preferably every 2 to 8 weeks, more preferably every 3 to 6 weeks, and even more preferably every 3 weeks.

Compositions, Unit Dosage Forms, and Kits

The present invention is also directed to kits comprising a first component comprising one or more epothilones of Formula I, Ia, Ib or Ic, or a pharmaceutically acceptable salt, solvate, clathrate, hydrate, or prodrug thereof and a second component comprising a pharmaceutically acceptable acid neutralizing buffer. The first component and the second component are provided as separate distinct pharmaceutical compositions which are intended to be administered separately. The first and second components are provided as a pharmaceutical dosage form suitable for oral administration or as solid pharmaceutical composition that can be constituted or reconstituted with a liquid to provide a liquid oral dosage form. Preferably, the epothilones of Formula I, Ia, Ib or Ic are packaged in light-protected vials.

Pharmaceutical compositions and dosage forms suitable for oral administration can be presented as discrete dosage forms, such as, but not limited to, tablets (e.g., chewable tablets), caplets, capsules, powder in a sachet, enteric coated tablets, enteric coated beads, enteric coated soft gel capsules, and liquids (e.g., flavored syrups). Such dosage forms contain predetermined amounts of the active ingredient and may be prepared by methods of pharmacy well known to those skilled in the art (See *Remington's Pharmaceutical Sciences,* 18th ed., Mack Publishing, Easton Pa. (1990)).

Typical oral dosage forms are prepared by combining the active ingredients in an intimate admixture with at least one excipient according to conventional pharmaceutical compounding techniques. Excipients can take a wide variety of forms depending on the form of preparation desired for administration. For example, excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents. Examples of excipients suitable for use in oral liquid dosage forms include, but are not limited to, water, glycols, oils, alcohols, flavoring agents, preservatives, and coloring agents.

Tablets and capsules represent convenient pharmaceutical compositions and oral dosage forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions and dosage forms of the invention is typically present in from about 50 to about 99 weight percent of the pharmaceutical composition or dosage form.

Disintegrants are used in the pharmaceutical compositions and dosage forms of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form the pharmaceutical compositions and solid oral dosage forms of the invention. The amount of disintegrant used varies based upon the type of formulation, and is readily discernible to those of ordinary skill in the art. Typical pharmaceutical compositions and dosage forms comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, TX), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The pharmaceutical compositions and dosage forms may further comprise one or more compounds that reduce the rate by which an active ingredient will decompose. Such compounds, which are referred to herein as "stabilizers," include, but are not limited to, antioxidants such as ascorbic acid and salt buffers.

Solutions for oral administration represent another convenient oral dosage form, in which case a solvent is employed. Liquid oral dosage forms are prepared by combining the active ingredient in a suitable solvent to form a solution, suspension, syrup, or elixir of the active ingredient in the liquid.

The solutions, suspensions, syrups, and elixirs may optionally comprise other additives including, but not limited to, glycerin, sorbitol, propylene glycol, sugars, flavoring agents, and stabilizers.

The kits of the invention may include the first and/or second components as an already prepared liquid oral dosage form ready for administration or, alternatively, may include the first and/or second components as a solid pharmaceutical composition that can be reconstituted with a solvent to provide a liquid oral dosage form. When the kit includes the first and/or second components as a solid pharmaceutical composition that can be reconstituted with a solvent to provide a liquid oral dosage form, the kit may optionally include the reconstituting solvent.

The constituting or reconstituting solvent is combined with the active ingredient to provide a liquid oral dosage form of the active ingredient. Preferably, the active ingredient is soluble in the solvent and forms a solution. The solvent may be water, a non-aqueous liquid, or a combination of a non-aqueous component and an aqueous component. Suitable non-aqueous components include, but are not limited to oils; alcohols, such as ethanol; glycerin; and glycols, such as polyethylene glycol and propylene glycol.

The pharmaceutically acceptable acid neutralizing buffers of the invention are preferably water soluble. Accordingly, the preferred solvent for the pharmaceutically acceptable acid neutralizing buffers is water or water based systems including saline solutions or dextrose solutions.

Some epothilones of Formula I, Ia, Ib or Ic, or a pharmaceutically acceptable salt, solvate, clathrate, hydrate, or prodrug thereof may be relatively insoluble in water.

Accordingly, for such epothilones of Formula I, Ia, Ib or Ic, or a pharmaceutically acceptable salt, solvate, clathrate, hydrate, or prodrug thereof, non-aqueous liquids or liquids that are a combination of a miscible aqueous component and a non-aqueous component are preferred with non-aqueous liquids being most preferred.

A preferred non-aqueous liquid for epothilones of Formula I, Ia, Ib or Ic, or a pharmaceutically acceptable salt, solvate, clathrate, hydrate, or prodrug thereof is surfactant such as propylene glycol and ethanol, preferably in a ratio of about 80:20. Suitable non-aqueous liquids or surfactants include, but are not limited to, polyethylene glycol, polysorbates, propylene glycol, glyceryl esters, Cremophor, fatty acid esters and alcohols, polyoxyethylene, and fatty alcohol esters and ethers.

When the solvent for the epothilones of Formula I, Ia, Ib or Ic, or a pharmaceutically acceptable salt, solvate, clathrate, hydrate, or prodrug thereof, includes an aqueous component, it is preferred that the aqueous component is buffered to reduce decomposition of the epothilone of Formula I, Ia, Ib or Ic. Liquid oral dosage forms comprising one or more epothilones of Formula I, Ia, Ib or Ic, or a pharmaceutically acceptable salt, solvate, clathrate, hydrate, or prodrug thereof, in an aqueous or partially aqueous solvent provides liquid oral dosage forms that are more stable than a liquid oral dosage form without a buffer. Specifically, it has been discovered that the rate of decomposition of one or more epothilones of Formula I, Ia, Ib or Ic, or a pharmaceutically acceptable salt, solvate, clathrate, hydrate, or prodrug thereof, in a buffered liquid oral formulation is less than the rate of decomposition in an unbuffered liquid oral formulation. Without wishing to be bound by theory, it is believed that epothilones of Formula I, Ia, Ib or Ic are unstable in acidic and basic medium, presumably as a result of an acid or base catalyzed hydrolytic opening of the epoxide ring. By buffering the liquid oral formulation, however, it is possible to maintain the pH of the liquid oral formulation at a value such the rate of decomposition of the epothilone of Formula I, Ia, Ib or Ic is slow enough that the epothilone of Formula I, Ia, Ib or Ic does not decompose before it can be administered to a patient. The aqueous or partially aqueous liquid oral dosage forms are preferably buffered to a pH of between about 5 to 9, preferably about 6 to 8.5, and more preferably about 7 to 8.

When the active ingredient is provided as a solid pharmaceutical composition that is constituted or reconstituted with a solvent to provide a liquid oral dosage form it is typically provided in powdered form and constituted with the liquid shortly before administration to the patient. The powdered pharmaceutical composition may be packaged, for example, in a vial to which is added the solvent. Alternatively, the contents of the vial may be added to the solvent in a separate container. The powdered active ingredient of the invention may also be packaged in a sachet, such as a foil package, that can be opened and the contents added to the solvent. The powdered active ingredient of the invention may also be formulated as a tablet that dissolves when it is added to the solvent. Often the tablet includes a disintegrant to facilitate dissolution of the tablet.

The present invention is also directed to pharmaceutical compositions comprising one or more epothilones of Formula I, Ia, Ib or Ic, or a pharmaceutically acceptable salt, solvate, clathrate, hydrate, or prodrug thereof, in solid form and a solid pharmaceutically acceptable acid neutralizing buffer in an amount sufficient to reduce decomposition of the one or more epothilones of Formula I, Ia, Ib or Ic, or a pharmaceutically acceptable salt, solvate, clathrate, hydrate, or prodrug thereof, when the pharmaceutical composition is reconstituted with a liquid to provide a liquid oral dosage form.

In addition to providing a more stable liquid oral dosage form, the pharmaceutical compositions of the invention also provide a liquid oral dosage form wherein the epothilone is more bioavailable when orally administered to a patient. Accordingly, the invention is also directed to a liquid oral dosage form comprising one or more epothilones of Formula I, Ia, Ib or Ic, or a pharmaceutically acceptable salt, solvate, clathrate, hydrate, or prodrug thereof, and a solid pharmaceutically acceptable acid neutralizing buffer dissolved in or dispersed in a solvent. Preferably, the one or more epothilones of Formula I, Ia, Ib or Ic, or a pharmaceutically acceptable salt, solvate, clathrate, hydrate, or prodrug thereof, and the solid pharmaceutically acceptable acid neutralizing buffer are dissolved in the liquid to provide a solution.

Preferably, the buffer is present in the pharmaceutical composition such that it provides a liquid oral formulation having a pH of between about 5 to 9, preferably about 6 to 8.5, and more preferably about 7 to 8. Typically, the pharmaceutically acceptable acid neutralizing buffer is present in an amount sufficient to deliver at least about 20 milliequivalents of acid neutralization capacity, preferably at least about 30 milliequivalents of acid neutralization capacity, more preferably at least about 40 milliequivalents of acid neutralization capacity, and most preferably at least about 50 milliequivalents of acid neutralization capacity when reconstituted with a liquid to provide the liquid oral dosage form. Any pharmaceutically acceptable acid neutralizing buffer that can provide a pH within this range may be used in the composition of the invention. Preferably, the pharmaceutically acceptable acid neutralizing buffer is a dibasic phosphate-monobasic phosphate buffer or a dibasic phosphate buffer-citric acid-citrate buffer.

Typically, the pharmaceutical compositions of the invention comprise the one or more epothilones of Formula I, Ia, Ib or Ic, or a pharmaceutically acceptable salt, solvate, clathrate, hydrate, or prodrug thereof, in a total amount of about 0.05 to about 200 mg, preferably from about 5 to about 100 mg, and more preferably about 10 to 50 mg.

The invention further relates to a kit comprising a pharmaceutical composition comprising (i) a combination of one or more epothilones of Formula I, Ia, Ib or Ic, or a pharmaceutically acceptable salt, solvate, clathrate, hydrate, or prodrug thereof, in solid form and a solid pharmaceutically acceptable acid neutralizing buffer and (ii) a solvent for reconstituting the pharmaceutical composition to provide a liquid oral dosage form, wherein the pharmaceutically acceptable acid neutralizing buffer is present in an amount sufficient to reduce decomposition of the one or more epothilones of Formula I, Ia, Ib or Ic, or a pharmaceutically acceptable salt, solvate, clathrate, hydrate, or prodrug thereof, when the combination is reconstituted with the solvent to provide the liquid oral dosage form.

The reconstituting solvent is combined with the active ingredient to provide a liquid oral dosage form of the active ingredient. The liquid oral dosage form may be a solution or a suspension. Preferably, the active ingredient is soluble in the solvent and forms a solution. The solvent may be water, a non-aqueous liquid, or a liquid that is a combination of a non-aqueous component and an aqueous component. Suitable non-aqueous components include, but are not limited to oils; alcohols, such as ethanol; glycerin; and glycols, such as polyethylene glycol and propylene glycol. A suitable solvent for use in the kit of the invention is propylene glycol:ethanol:phosphate buffer (0.1–1M, pH 7–8) in a ratio of about 58:12:30.

The solvent may further comprise one or more additional additives such as, but not limited to, glycerin, sorbitol, propylene glycol, flavoring agents, and preservatives to improve the palatability of the liquid oral dosage form.

This invention further encompasses anhydrous pharmaceutical compositions and dosage forms comprising the active ingredients, i.e., the one or more epothilones of Formula I, Ia, Ib or Ic, or a pharmaceutically acceptable salt, solvate, clathrate, hydrate, or prodrug thereof and/or the pharmaceutically acceptable acid neutralizing buffer. Anhydrous pharmaceutical compositions and dosage forms are advantageous since water can facilitate the degradation of some compounds. For example, the addition of water (e.g., 5%) is widely accepted in the pharmaceutical arts as a means of simulating long-term storage in order to determine characteristics such as shelf-life or the stability of formulations over time (See, e.g., Jens T. Carstensen, *Drug Stability: Principles & Practice,* 2d. Ed., Marcel Dekker, NY, N.Y., 1995, pp. 379–80). In effect, water and heat accelerate the decomposition of some compounds. Thus, the effect of water on a formulation can be of great significance since moisture and/or humidity are commonly encountered during manufacture, handling, packaging, storage, shipment, and use of formulations. Anhydrous pharmaceutical compositions and dosage forms are especially advantageous for pharmaceutical compositions and dosage forms comprising one or more epothilones of Formula I, Ia, Ib or Ic, or a pharmaceutically acceptable salt, solvate, clathrate, hydrate, or prodrug thereof, since these compounds are sensitive to moisture.

Anhydrous pharmaceutical compositions and dosage forms should be prepared and stored such that its anhydrous nature is maintained. Anhydrous pharmaceutical compositions and dosage forms of the invention can be prepared using anhydrous or low moisture containing ingredients and low moisture or low humidity conditions. Anhydrous pharmaceutical compositions and dosage forms are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

EXAMPLES

Certain embodiments of the present invention, as well as certain advantages of the present invention, are illustrated by the following non-limiting examples.

Example 1

Pharmacology: Drug Administration

For administration of Compound A to rodents, two different excipients have been used: (1) ethanol/water (1:9, v/v) and (2) Cremophor®/ethanol/water (1:1:8, v/v). Compound A was first dissolved in ethanol or a mixture of Cremophor®/ethanol (50:50). Final dilution to the required dosage strength is made less than 1 hr before drug administration. For parenteral administration (IV), dilution was made with water so that the dosing solutions contain the specified excipient composition described above. For oral administration (PO), the dilution was made with 0.25 M sodium phosphate buffer (pH=8.0) at a ratio of 30/70, v/v. Paclitaxel was dissolved in a 50/50 mixture of ethanol and Cremophor® and stored at 4° C.; final dilution of paclitaxel was obtained immediately before drug administration with NaCl 0.9%. Fresh preparation of paclitaxel was necessitated by precipitation. The volume of all compounds injected was 0.01 ml/gm for mice and 0.005 ml/gm for rats.

Example 2

Pharmacology: Chemicals and Supplies

Unless specified, chemicals and solutions used for the maintenance of cell culture were obtained from GIBCO/BRL. Sterile tissue culture ware was obtained from Corning, N.Y. All other reagents were from Sigma or Fisher at the highest grade available.

Example 3

Pharmacology: Tumor Cell Lines

HCT116 human carcinoma cell lines and HCT116/VM46 cells, a MDR variant[1], were maintained in McCoy's 5A medium (GIBCO) and 10% heat inactivated fetal bovine serum (GIBCO). A2780 human ovarian carcinoma cells and A2780Tax cells obtained from Dr. Antonio Fojo (NCI, Bethesda, Md.) were maintained in IMEM (GIBCO) and 10% fetal bovine serum (GIBCO). This paclitaxel resistant cell line does not overexpress P-glycoprotein but has point mutations in the M40 isotype of beta-tubulin[2]. Purified tubulin isolated from these resistant cells is refractory to polymerization by paclitaxel and is thought to account for the resistance to this drug, and collateral sensitivity to microtubule depolymerizing agents, such as vinblastine.

Example 4

Pharmacology: Cytotoxicity Assay

The in vitro cytotoxicity was assessed in tumor cells by a tetrazolium-based colorimetric assay which takes advantage of the metabolic conversion of MTS (3-(4,5-dimethylthiazol-2-yl)-5-(3-carboxymethoxyphenyl)-2-(4-sulphenyl)-2H-tetrazolium, inner salt) to a reduced form that absorbs light at 492 nm. Cells were seeded 24 hr prior to drug addition. Following a 72-hour incubation at 37° C. with serially diluted compound, MTS, in combination with the electron coupling agent phenazine methosulfate, was added to the cells. The incubation was continued for 3 hours, then the absorbancy of the medium at 492 nm was measured with a spectrophotometer to obtain the number of surviving cells relative to control populations. The results are expressed as median cytotoxic concentrations ($IC_{50}$ values).

Example 5

Pharmacology: Tubulin Polymerization Assay

The potency with which Compound A and paclitaxel polymerize tubulin isolated from calf brain was evaluated by published techniques (Long, B. H. and Fairchild, C. R., Cancer Res., 1994, 54, 4355–4361; and Williams, R. C. and Lee, J. C., Methods in Enzymology, 1982, 85, 376–385).

Example 6

Pharmacology: Animals

All rodents were obtained from Harlan Sprague Dawley Co. (Indianpolis, Ind.), and maintained in an ammonia-free environment in a defined and pathogen-free colony. The animal care program of Bristol-Myers Squibb Pharmaceutical Research Institute is fully accredited by the American Association for Accreditation of Laboratory Animal Care (AAALAC).

Example 7

Pharmacology: In Vivo Antitumor Testing

The following human tumors were used: A2780 ovarian, A2780Tax ovarian (established from cells obtained from Dr.

Antonio Fojo, Medicine Branch, NCI, Bethesda, Md.), HCT116/VM46 colon, Pat-7 ovarian (established from a tumor biopsy provided by Dr. Thomas Hamilton, Fox Chase Cancer Center, Philadelphia, Pa., from a patient who had developed resistance to TAXOL®) and Pat-26 pancreatic carcinoma (from a liver metastasis biopsy provided by Dr. John Hoffman, Fox Chase Cancer Center, Philadelphia, Pa.).

The human tumors were maintained in Balb/c nu/nu nude mice. Tumors were propagated as subcutaneous transplants in the appropriate mouse strain using tumor fragments obtained from donor mice. All tumor implants for efficacy testing were subcutaneous (sc).

The required number of animals needed to detect a meaningful response were pooled at the start of the experiment and each was given a subcutaneous implant of a tumor fragment (≈50 mg) with a 13-gauge trocar. For treatment of early-stage tumors, the animals were again pooled before distribution to the various treatment and control groups. For treatment of animals with advanced-stage disease, tumors were allowed to grow to the pre-determined size window (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2-Wt1) provides a measure of treatment-related toxicity.

Tumor response was determined by measurement of tumors with a caliper twice a week, until the tumors reach a predetermined "target" size of 1 gm. Tumor weights (mg) were estimated from the formula:

Tumor weight=(length×width$^2$)÷2

Antitumor activity was evaluated at the maximum tolerated dose (MTD) which is defined as the dose level immediately below which excessive toxicity (i.e. more than one death) occurred. The MTD was frequently equivalent to OD. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T–C value), defined as the difference in time (days) required for the treated tumors (T) to reach a predetermined target size compared to those of the control group (C).

To estimate tumor cell kill, the tumor volume doubling time was first calculated with the formula:

TVDT=Median time (days) for control tumors to reach target size–Median time (days) for control tumors to reach half the target size and Log cell kill=$T$–$C$÷(3.32×$TVDT$)

Statistical evaluations of data were performed using Gehan's generalized Wilcoxon test[6].

Example 8

Pharmacology: Intravenous Infusion

Constant-rate infusional drug delivery via the tail vein was accomplished using the L-CATH® Neonatal Catheter System (Luther Medical Products, Inc., Tustin, Calif.). The 28 Ga (0.4 mm O.D.) catheter was inserted in the tail vein approximately 5 cm from the base and advanced 4 cm into the vein. The catheter was stabilized with Nexaband Liquid (Henry Schein Inc.) and then firmly secured with Tegaderm (Henry Schein, Inc.). The entire tail and catheter was then inserted into a protective sheath and then tied to a swivel. Mice were freely moving during the entire infusion period.

Example 9

Pharmacology: Quantitation of Compund a by HPLC/MS/MS

Plasma samples (25 μl) were de-proteinized with three volumes of acetonitrile containing 5 μg/ml of BMS-263966 as internal standard (IS). After centrifugation to remove precipitated proteins, a 10 μl portion of clear supernatant was analyzed by HPLC/MS/MS. The HPLC system consisted of a Hewlett Packard model 1100 HPLC with HP Autosampler model G1313A. The column used was a Phenomenex Luna C18-ODS(3), 2 mm×50 mm, 3 uM particles, maintained at 60° C. at a flow rate of 0.5 ml/min. The mobile phase consisted of 5 mM ammonium acetate in 90% water/10% acetonitrile (A) and 5 mM ammonium acetate in 10% water/90% acetonitrile (B) at pH=5.0. The initial mobile phase composition was 100% A/0% B. After sample injection, the mobile phase was changed to 30% A/70% B over 1 minute, and held at that composition for an additional 4 minutes. The mobile phase was then returned to initial conditions, and the column re-equilibrated. The HPLC was interfaced to a Finnigan LCQ ion-trap mass spectrometer operated in the positive electrospray, full MS/MS mode. For Compound A, fragmentation of m/z 523 yielded daughter ions for quantitation at m/z's 335, 417, and 435. For the internal standard, m/z 594 was fragmented to yield daughter ions for quantitation at m/z 406. Helium was the collision gas. The retention times for Compound A and the IS were 3.2 and 5.0, respectively. The standard curve ranged from 10 nM to 40 μM and was fitted with a quadratic regression weighted by reciprocal concentration (1/x). LOQ for the purposes of this assay was 25 nM. QC samples at two levels in the range of the standard curve were used to accept individual analytical sets.

Example 10

Pharmacology: In Vitro Safety Pharmacology

Human embryonic kidney (HEK293) cells stably transfected with the human ether-a-go-go related gene (HERG) cDNA were utilized in the HERG assay. Rabbit Purkinje fibres were used for the Purkinje-fibre action potential assay[7].

Example 11

Pharmacology Results: Cytotoxicity Against Cancer Cells In Vitro

Compound A has a broad spectrum of activity against a panel of tumor cell lines in vitro. Of the 8 cells lines tested (FIG. 1), 7 have $IC_{50}$ values between 0.9–3.5 nM. The highly multi-drug resistant (MDR) colon tumor lines HCT116/VM46 has an $IC_{50}$ of 11.9 nM. It should be noted that Compound A did substantially "overcome" the multi-drug resistance inherent in the HCT/VM46 cells. Thus, for paclitaxel, the ratio of concentration (R/S, or resistance ratio) required to inhibit cell growth by 50% in this resistant line versus that required for the sensitive HCT116 line was 155 fold. In comparison, the R/S ratio for Compound A was only 12.8.

Example 12

Pharmacology Results: Tubulin Polymerization

The cytotoxic activities of the epothilones, like those of the taxanes, have been linked to stabilization of microtubules which results in mitotic arrest at the $G_2/M$ transition[8]. In this regard the potency of Compound A is similar to those of its two natural analogs, epothilones A and B, as well as to an epothilone of formula Id (Compound B), an epothilone analog that is currently in clinical development (Table 1).

TABLE 1

Tubulin Polymerization Potency of Four Epothilones Relative to Paclitaxel

| Analog | Polymerization Potency, $EC_{0.01}$ ($\mu M$) | Ratio of Polymerization Potency of Analog/Paclitaxel |
| --- | --- | --- |
| Compound A | 7.4 | 1.7 |
| Compound B | 3.5 | 0.4 |
| BMS-212188 (Epothilone A) | 2.0 | 0.4 |
| BMS-205535 (Epothilone B) | 1.8 | 0.3 |

Compound B is [1S-[1R*,3R*(E),7R*,10S*,11R*,16S*]]-7,11-dihydroxy 8,8,10,12,16-pentamethyl-3-[1-methyl-2-(2-methyl-4-thiazolyl)ethenyl-17-oxa-4-azabicyclo[14.1.0]heptadecane-5,9-dione (BMS-247550), and is depicted below:

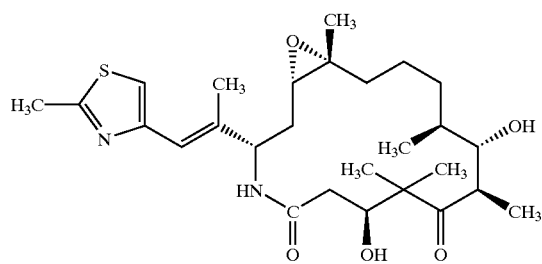

Example 13

Pharmacology Results: Antitumor Activity by Parenteral Administration to Mice Compound A was evaluated in a panel of five human tumor xenografts chosen because of their resistance to paclitaxel (Table 2). The antitumor efficacy of Compound A was compared head-to-head with concomitantly tested IV Compound B in each of the models described. Compound B, shown below, is a related epothilone B analog which is currently in clinical Phase I trials.

TABLE 2

Tumor Model Characteristics

| Tumor | Histology | Paclitaxel sensitivity | Resistance Mechanism(s) |
| --- | --- | --- | --- |
| Human | | | |
| Pat-7 | Ovarian | Resistant[1] | MDR, MRP[2] |
| A2780Tax | Ovarian | Resistant | Tubulin mutation |
| HCT116/VM46 | Colon | Resistant | MDR |
| Pat-21 | Breast | Resistant[1] | Unknown |
| Pat-26 | Pancreatic | Refractory | Unknown |

[1]Clinical resistance to TAXOL
[2]MRP = multidrug resistance related protein

1. Pat-7 Clinically-Derived TAXOL®-Resistant Ovarian Carcinoma Model

This tumor model was established from a tumor biopsy of an ovarian cancer patient (Pat-7), who was initially responsive to TAXOL® treatment but ultimately developed resistance to it following nine courses of monotherapy with TAXOL®. Prior to treatment with TAXOL®, Pat-7 also received numerous other chemotherapeutic agents including carboplatin, cytoxan, VP-16, ifosfamide and altretamine. A tumor biopsy was taken following development of TAXOL® resistance.

Compound A was administered to nude mice bearing staged tumors using an every 4 days×3 (Q4D×3) schedule. At optimal dose (8 mg/kg/inj), it was highly active eliciting 2.4 (Table 3 and FIG. 2A). Concomitantly evaluated IV Compound B yielded 1.8 LCK, respectively. It is of note that Compound A demonstrated robust activity in this paclitaxel-resistant model, yielding active results (i.e. >1 LCK) at dose levels considerably less than the MTD (FIG. 2B).

2. A2780Tax Human Ovarian Carcinoma Xenograft (Mutated Tubulin)

A2780Tax is a paclitaxel-resistant human ovarian carcinoma model. It was derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein[2].

Figure 3:
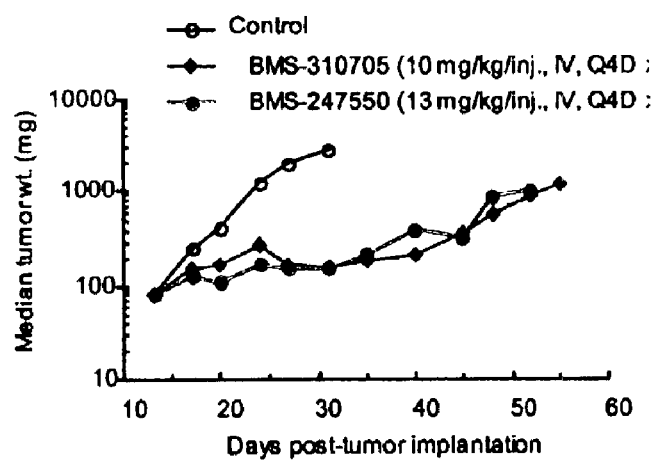
FIG. 3 shows comparative antitumor activity of oral epothilone of formula Ic and IV epothilone of formula Id in the A2780Tax human ovarian carcinoma model. The compounds were administered at the indicated doses, every 4 days for a total of 3 administrations starting 13 days after tumor implantation Q4D×3;13). Each datum point represents the median tumor weight of 8 mice.

Compound A administered to mice bearing staged tumors on a Q4D×3 schedule yielded 3.6 LCK at its MTD (10 mg/kg/inj). In comparison, IV Compound B yielded 3.5 LCK at its MTD (Table 3 and FIG. 3).

3. HCT116/VM46 Human Colon Carcinoma Xenograft (Multi-Drug Resistant

HCT116/VM46 is an MDR-resistant colon carcinoma developed from the sensitive HCT116 parent line. In vivo, grown in nude mice, HCT116/VM46 has consistently demonstrated high resistance to paclitaxel[9].

Compound A treatment of mice bearing staged HCT116/VM46 tumors using a Q4D×3 schedule produced significant antitumor effects. At its optimal dose Compound A yielded 1.5 LCK. Concomitantly tested IV Compound B yielded 1.3 LCK at its MTD (Table 3).

4. Pat-21, Clinically-Derived Paclitaxel Resistant Breast Cancer Model

Pat-21 is an early passage paclitaxel-resistant tumor model established from a tumor biopsy of a breast cancer patient with metastatic disease who was given, and failed to respond to, an experimental therapy consisting of 5 cycles of TAXOL® in combination with the multidrug resistance reversal agent dexverapamil. Prior to TAXOL® therapy, the patient also received chemotherapy consisting of adriamycin, cytoxan, methotrexate and 5-FU. Tumor biopsies were obtained after cessation of TAXOL® therapy.

Pat-21 grows at a relative slow rate in nude mice, doubling in volume approximately every 3 weeks. For antitumor efficacy evaluation, two courses of Compound A or Compound B were administered to mice bearing Pat-21 tumors staged to approximately 100 mg. The two courses were separated by a 3-week interval. Each course consisted of 3 doses given every 4 days. Compound A was highly active against this model yielding >4.1 LCK at its MTD of 9 mg/kg/inj. In comparison, Compound B was also highly active, yielding LCK value of 3.9 LCK at its optimal dose (Table 3).

5. Pat-26 Human Pancreatic Carcinoma Model

Pat-26 is a human pancreatic carcinoma xenograft model established from a liver metastasis of a patient with metastatic pancreatic cancer. The biopsy was obtained at diagnosis and the patient had no prior therapy. Compound A and Compound B were equally active yielding 1.2 LCK at its MTD (10 mg/kg/inj, every 4 days×3) (Table 3).

TABLE 3

Preclinical Antitumor Activity of Compound A and
Paclitaxel Versus Paclitaxel-Resistant Tumors

| Tumor | Rt., schedule | Compound A OD[1] (mg/kg) | LCK[2] | Compound B LCK[2] | PACLITAXEL LCK[2] |
|---|---|---|---|---|---|
| Human tumors-in nude mice | | | | | |
| Pat-7 | IV, QD × 3 | 8 | 2.4 | 1.8 | 0.8[3] |
| A2780Tax | IV, QD × 3 | 10 | 3.6 | 3.5 | 0.8[3] |
| HCTVM46 | IV, QD × 3 | 7.5 | 1.5 | 1.3 | 0.55[3] |
| Pat-21 | IV, QD × 3; 37, 66 | 9 | >4.1 | 3.9 | 0.3[3] |
| Pat-26 | IV, QD × 3 | 10 | 1.2 | 1.2[3] | 0.4 |

[1]OD, optimal dose or maximum tolerated dose (MTD).
[2]LCK, gross log cell kill, are for MTD, or highest dose tested if inactive.
[3]Results were obtained in separate studies from that reported for Compound A

Example 14
Pharmacology Results: Effects of Formulation

Compound A is a chemically stable epothilone analog which is also highly water-soluble. For these reasons Compound A may be formulated in an entirely aqueous excipient system for parenteral administration. To determine whether differences in the dosing vehicle may affect the antitumor activity of Compound A, a direct head-to-head comparison of the antitumor efficacy of Compound A formulated in either cremophor/ethanol/water (10:10:80, v/v/v) or sodium acetate buffer (30 mM, pH 5.0) was conducted. No formulation related effect was observed. Compound A formulated in either vehicle was equally active, yielding 3.3 and 3.4 LCK's, respectively.

Figure 4:
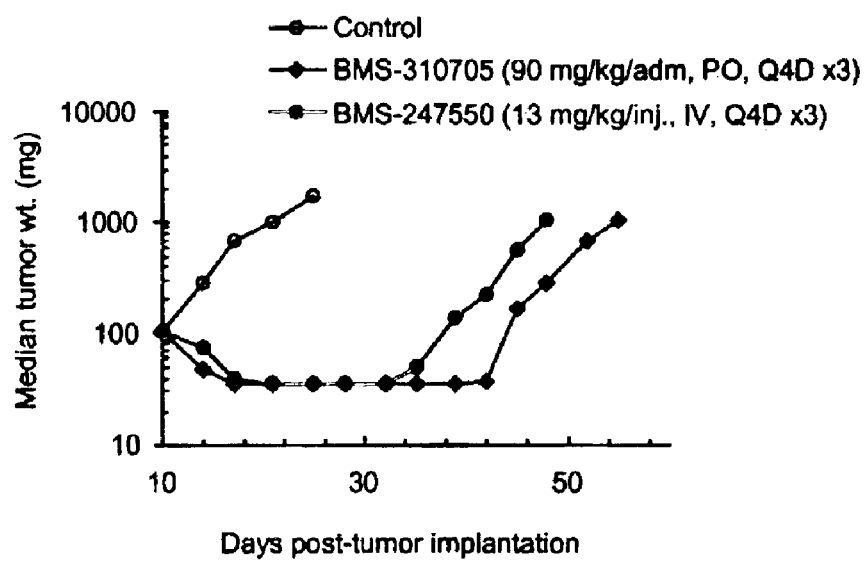
FIG. 4 shows comparative antitumor activity of oral epothilone of formula Ic and IV epothilone of formula Id in the Pat-7 human ovarian carcinoma model. The compounds were administered at the indicated doses, every 4 days for a total of 3 administrations starting 10 days after tumor implantation Q4D×3;10). Each datum point represents the median tumor weight of 8 mice.

Example 15
Pharmacology Results: Antitumor Activity by Oral Route of Administration The fact that Compound A is significantly more stable at neutral pH than at low pH provided the impetus for the evaluation of Compound A by oral administration (PO) in a pH buffering vehicle (0.25M potassium phosphate, pH 8.0). Using a Q4D×3 schedule, Compound A was highly active orally against the Pat-7 human ovarian carcinoma model, yielding 2.4 LCK at its MTD (FIG. 4 and Table 4). In comparison, concomitantly tested IV Compound B produced 1.9 LCK at its optimal dose and schedule.

TABLE 4

Antitumor Activity of Oral compound A and IV Compound B

| Tumor | Expt. No. | Compound A (PO) Rt., schedule | OD[1] (mg/kg) | LCK[2] (cures/total) | Compound B (IV) LCK[2] |
|---|---|---|---|---|---|
| Pat-7 | 18 | PO, QD × 3 | 90 | 2.4 | 1.9 |

[1]OD, optimal dose or maximum tolerated dose (MTD).
[2]LCK, gross log cell kill.

Example 16
Pharmacology Results: Antitumor Activity by Parenteral Administration to Rats Compound A was evaluated versus the human ovarian carcinoma xenograft A2780 grown in nude rats. Compound A only demonstrated modest activity (0.7 LCK) in the manner tested at its MTD (3 mg/kg/inj., IV, every 8 days×2). In comparison, Compound B produced 3.3 LCK at its MTD (2.4 mg/kg/inj, IV, every 8 days×2).

Figure 5:
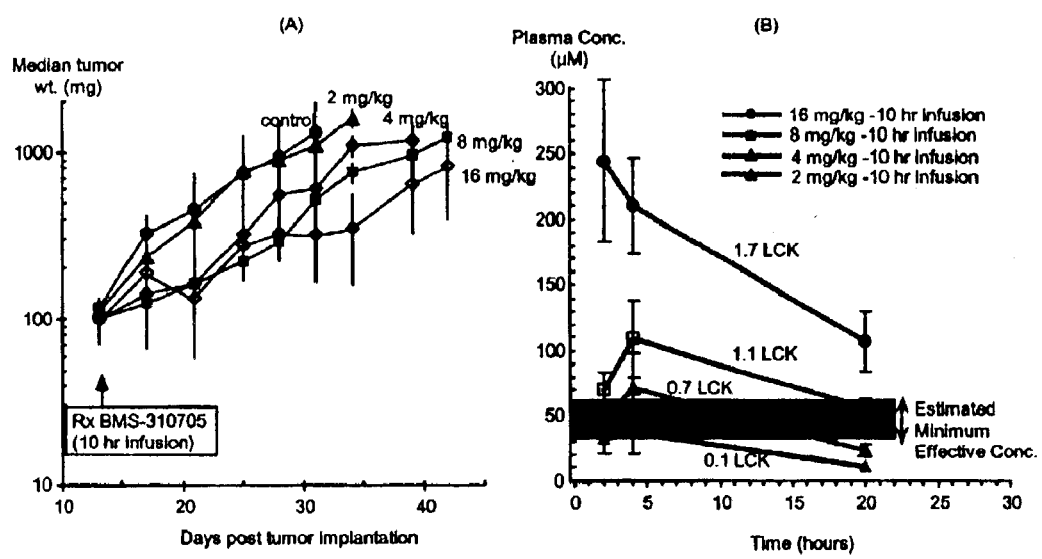
FIG. 5.

Example 17
Pharmacology Results: Minimum Effective Infusional Dose Regimen of Compound A Versus sc Pat-7 Human Ovarian Carcinoma An experiment was conducted in the sc Pat-7 model to determine the minimum effective infusional dose Compound A required to achieve antitumor activity. In this study, mice bearing Pat-7 tumors were administered, by constant-rate IV infusion over 10 hr, Compound A at 4 different dose levels (2, 4, 8, 16 mg/kg). At these dose levels, a range of antitumor activities, which were clearly dose-dependent, were observed: Tumor growth delay equivalent to LCK values of 0.1 (P=0.79, not significant), 0.7 (P=0.019, significant), 1.1 (P=0.004, significant), and 1.7 (P=0.001, significant) were observed for 2, 4, 8 and 16 mg/kg, respectively (FIG. 5A). From these data, it is concluded that the minimum effective dose (MED) for Compound A (to yield 0.5 LCK) is between 2 and 4 mg/kg.

In parallel, the corresponding plasma apparent steady-state concentrations (Css) at each dose level was determined (FIG. 5B). From these data, the MEC for Compound A was estimated to be in the range 35–60 nM.

Example 18
Pharmacology Results: in Vitro Safety Pharmacology

1. HERG (IKr Current) Assay

In a non-GLP study[7], Compound A was evaluated for effects on potassium channel current at concentrations of 10 and 30 μM. The human ether-a-go-go related gene (HERG) encodes the rapidly activating delayed-rectifier potassium channel (IKr) in heart. Compound A weakly blocked IKr current in a dose dependent manner with a maximum inhibition of 13.5% at a concentration of 30 μM. Based on the findings, it is unlikely that Compound A would cause IKr-mediated increases in the QT interval at anticipated therapeutic plasma concentrations.

2. Rabbit Purkinje-Fiber Model

In a non-GLP study[7], Compound A, at concentrations of 3, 10 and 30 μM, was evaluated in an in vitro rabbit Purkinje fiber model. This model was developed to determine if a compound would affect the action-potential duration of the Purkinje fiber or other action-potential parameters. Compound A minimally decreased Purkinje fiber APD90 (less than 10%) at a concentration of 30 μM. Based on these findings, Compound A is unlikely to provoke clinically relevant electrocardiographic effects in vivo.

References (For Examples 1–18)

1. Long, B. H., Wang, L., Lorico, A., et al. Mechanisms of resistance to etoposide and teniposide in acquired resistant human colon and lung carcinoma cell lines. Cancer Res., 1991. 51: 5275–5284.
2. Giannakakou, P., Sackett, D. L., Kang, Y. K., et al. Paclitaxel-resistant human ovarian cancer cells have mutant beta-tubulins that exhibit impaired paclitaxel-driven polymerization. J. Biol. Chem., 1997. 272: 17118–25.
3. Riss, T. L. and Moravec, R. A. Comparison of MTT, XTT, and a novel tetrazolium compound MTS for in vitro proliferation and chemosensitivity assays. Mol. Biol. Cell, 1992. 3 (suppl.): 184a.
4. Long, B. H. and Fairchild, C. R. Paclitaxel inhibits progression of mitotic cells to G(1) phase by interference with spindle formation without affecting other microtubule functions during anaphase and telephase. Cancer Res., 1994. 54: 4355–4361.
5. Williams, R. C. and Lee, J. C. Preparation of tubulin from brain. Methods in Enzymology, 1982. 85: 376–385.
6. Gehan, G. A. A generalized Wilcoxon test for comparing arbitrarily singly-censored samples. Biometrika, 1985. 52: 203–233.
7. Levesque, P. C. BMS-310705: Effects on HERG/IKr currents and rabbit purkinje-fibre action potentials. Bristol-Myers Squibb Pharmaceutical Research Institute, 7 Nov. 2000. Document Control No. 920009044 VD-v1.0.
8. Bollag, D. M., McQueney, P. A., Zhu, J., et al. Epothilones, a new class of microtubule-stabilizing agents with a Taxol-like mechanism of action. Cancer Res., 1995. 55: 2325–2333.
9. Lee, F. Y. F. Preclinical Pharmacology of BMS-310705, an Epothilone Analog. Bristol-Myers Squibb Pharmaceutical Research Institute, 4 Dec. 2000. Document Control No. 920009170 VD-v1.0.

Example 19

Pharmacokinetics: Analytical Methods

The man pharmacokinetic parameters of Compound A in preclinical studies is shown in FIGS. 6(A) and 6(B).

Plasma samples from exploratory pharmacokinetic studies were analyzed for Compound A concentrations using an LC/MS/MS assay with a standard curve range of 3.9 to 2000 ng/mL. In pharmacodynamic studies, Compound A concentrations were determined using an LC/MS/MS assay with a standard curve range of 10–40000 nM (5.23–20920 ng/mL) in mouse plasma. For toxicology studies, validated LC/MS/MS assays were used to determine the concentrations of Compound A in rat and dog plasma. Analytical data management for the validated assays was carried out using Watson®. The standard curve range for the validated assay in both matrices was 2 to 500 ng/mL of Compound A. The coefficient of variation for the inter- and intra-assay precision in rat and dog plasma was within 9% and the accuracy was greater than 92%. Compound A was found to be stable for at least 4 h at room temperature in rat EDTA plasma and for at least 4 h at 4EC in dog EDTA plasma prior to processing for analytical work, and for at least 5 days at 4EC in an autosampler after processing. Compound A was stable for at least 4 months at !20EC and through at least 3 freeze-thaw cycles in rat and dog EDTA plasma. In addition, Compound A was stable in fresh rat and dog EDTA whole blood for at least 1 h at 4EC.

Example 20

Pharmacokinetics: In Mice

The pharmacokinetics of Compound A was evaluated in nude mice after IV (5 mg/kg) and oral (15 mg/kg) administration (n=15 mice/group). Compound A was dissolved in a mixture of cremophor:ethanol:water (10:10:80) and cremophor:ethanol:phosphate buffer, pH 8 (10:10:80) for the preparation of IV and oral doses, respectively. Plasma concentrations of Compound A were determined at 10 and 45 min, and 2, 4, and 6 hours postdose from 3 mice/time point/group. Composite plasma concentration-time profiles were constructed for pharmacokinetic analysis. The CLT of Compound A in nude mice was 152 mL/min/kg, which is greater than the reported liver plasma flow of about 54 ml/min/kg. The VSS values was 38 L/kg which is greater than total body water of about 0.7 L/kg, indicating significant extravascular distribution. The T-HALF value, both after IV and oral administration, was 3.3 h. The absolute oral bioavailability of Compound A in mice was 21%.

Example 21

Pharmacokinetics: In Rats

1. Single Dose Pharmacokinetic Studies

The pharmacokinetics of Compound A were investigated in fasted male Sprague-Dawley rats following single intraarterial (IA) (2 mg/kg; 10 min infusion) and oral (8 mg/kg) administration. A total of eight rats were divided into four groups (three IA groups and one oral group), with two rats in each group. For the three IA groups, Compound A was prepared in three different dosing solutions: vehicle 1, ethanol:water (10:90); vehicle 2, cremophor:ethnaol:water (10:10:80); and vehicle 3, propylene glycol:ethanol: phosphate buffer, 0.05 M, pH 7.4 (40:5:55). The vehicle used for the oral administration was propylene glycol:ethanol::phophate buffer, 1 M, pH 8 (58:12:30). Plasma concentrations of Compound A were determined at 10, 15, 30, and 45 min, and at 1, 2, 4, 6, 8, and 10 hours after dosing. The mean AUC values for IA doses administered with vehicles 1, 2, and 3 were 133, 708, 210 h.ng/mL, respectively, suggesting that the presence of cremophor in the formulation resulted in a marked increase (about 3.4- and 5.3-fold higher when compared to vehicles 1 and 3, respectively) in systemic exposure. The increase in systemic exposure with the cremophor-based formulation is presumably due to the formation of micelles by cremophor which can entrap Compound A similar to that apparent with paclitaxel formulation containing cremophor. The absolute oral bioavailability of Compound A in rats was 28% (using the dose given with vehicle 3 as the reference).

In another pharmacokinetic study, fasted male Sprague-Dawley rats, assigned to two IA groups (2 mg/kg) and one oral (8 mg/kg) group (n=3/group), were administered a single dose of Compound A. Compound A was prepared for IA administration in two separate vehicles: vehicle 1, cremophor:ethanol:water (10:10:80), and vehicle 2, ethanol::phosphate buffer, 0.05 M, pH 7.4 (6:94). The vehicle for the oral administration was ethanol:phosphate buffer, 0.3 M, pH 8 (18:82). Samples were collected at 10, 15, 30, and 45 min, and at 1, 2, 4, 6, 8, 10, 24, and 48 hours after dosing. The mean AUC values for IA doses, administered with vehicles 1 and 2, were 2889 and 717 h.ng/mL, respectively, confirming that the presence of cremophor in the IA formulation results in a marked increase (about 4-fold) in the systemic exposure presumably due to formation of micelles than entrap Compound A. The absolute oral bioavailability of Compound A in rats in this study was 34% (using the dose given with vehicle 2 as the reference).

2. Single Dose Toxicity Study

The single dose IV toxicokinetics of Compound A in rats were evaluated as a part of a toxicology study. Compound A, prepared in 50 mM citrate buffer (pH 5), was given intravenously (over approximately 1–2 min period) at doses of 1, 5, and 7 mg/kg to 3 rats/gender/dose. Blood samples were collected at 3, 15, and 30 minutes, and at 1, 3, 6, 12, and 24 h after dosing. Plasma concentrations of Compound A were determined using a validated LC/MS/MS assay with a standard curve range of 2–500 ng/mL. Across doses and sex, CMAX values ranged from 183 to 3914 ng/mL and AUC values ranged from 159 to 1938 h.ng/mL. For doses in a ratio of 1:5:7, the mean CMAX values of Compound A in males and females were in the ratio of 1:10:19 and 1:11:19, respectively, and the AUC values were in the ratio of 1:4.2:7.8 and 1:8.0:12, respectively. Systemic exposures were reasonably similar between male and female rats. In conclusion, a dose-related increase in the systemic exposure to Compound A was observed, with the increase being more than the dose increment. Furthermore, there appeared to be no differences in the toxicokinetics of Compound A between male and female rats.

Example 22

Pharmacokinetics: In Dogs

1. Single Dose Pharmacokinetic Study

The pharmacokinetics of Compound A were investigated in fasted male beagle dogs (n=3) after an IV (0.5 mg/kg, as a 10 min infusion) and oral (1 mg/kg) dose of Compound A in a cross-over design. The vehicle used for both IV and oral dose was propylene glycol:ethanol:phosphate buffer (pH 7.4–8.0) (40:5:55). Plasma samples were collected at 10, 15, 30, and 45 min, and at 1, 2, 4, 6, 8, 12, and 24 hours after dosing, and the concentrations of Compound A were determined. After IV administration, the CLT of Compound A in dogs was about 25.7 mL/min/kg which is greater than the reported liver plasma flow of about 19 mL/min/kg in dogs. The VSS value after IV administration was 4.7 L/kg, which is greater than the reported total body water of 0.6 L/kg in dogs, indicating significant extravascular distribution of Compound A. The T-HALF of Compound A was 3.9 and 3.1 h after IV and oral administration, respectively. The mean absolute oral bioavailability of Compound A in dogs was 40%.

2. Single Dose Toxicokinetic Study

The single dose IV toxicokinetics of Compound A were evaluated in dogs as a part of a toxicology study. Compound A, prepared in 50 mM citrate buffer (pH 5), was given by IV infusion (over approximately 2–3 min period) at nominal doses of 0.07 and 0.35 mg/kg (the actual doses were 0.055 and 0.27 mg/kg, respectively) to 2 dogs/sex/dose. Blood samples were collected at 5 and 30 minutes, and at 1, 3, 6, 12, and 24 h after dosing. Plasma concentrations of Compound A were determined using a validated LC/MS/MS assay with a standard curve range of 2–500 ng/mL. For the 0.055 and 0.27 mg/kg doses, mean CMAX values, combined across gender (due limited sample size), were 104 and 664 ng/mL, respectively, and AUC values were 48.3 and 362 h.ng/mL, respectively. For actual doses in a ratio of 1:4.9, the mean CMAX and AUC values of Compound A were in the ratio of 1:6.4 and 1:7.5, respectively. Definitive comparison between sex was not made due to limited sample size per sex; however, it appeared that there were no marked differences in the systemic exposure to Compound A between male and female dogs. In conclusion, a dose-related increase in the systemic exposure to Compound A was observed, with the increase being more than the dose increment.

Example 23

Oral Bioavailability in Humans

Compound A was administered to human patients (n=10) at a dose of 40 mg/m² by the IV and oral routes and the oral bioavailability was determined. Compound A was well absorbed orally, providing a favorable drug exposure profile that is consistant with efficacious exposure in preclinical cancer models.

| Oral Pharmacokinetics of Compound A in Humans | |
|---|---|
| No. of Subjects (n) | 10 |
| Tmax, hr | 1.0 (0.5, 1.5)* |
| Cmax, ng/mL (SD) | 177 (104) |
| AUC, ng.hr/mL (SD) | 631 (478) |
| Half-Life, hr (SD) | 29.8 (16.2) |
| Bioavailability, % (SD) | 27 (13)** |

*median (minimum, maximum).
**n = 9, bioavailability not evaluable in 1 patient that did not receive intravenous dose.

Example 24

Pharmacokinetics: in Vitro Studies

1. Caco-2 Permeability

Permeability studies with Compound A were conducted using Caco-2 monolayers. The permeability coefficient (Pc) of Compound A was 60 nm/sec at 105000 ng/mL (200 μM). Compounds that have Pc values ~50 nm/sec have widely varying extents of absorption in humans, ranging from 15% to 95% (mannitol, Pc=32 nm/sec, 15% absorbed; acebutalol, Pc=48 nm/sec, 40% absorbed; cimetidine, Pc=49 nm/sec, 95% absorbed). Hence, it was not possible to make reliable predictions regarding oral absorption of Compound A in humans.

2. In Vitro Metabolism (a) Microsomal Incubations

Upon incubation of Compound A (10500 ng/mL; 20 μM) with mouse, rat, dog, and human liver microsomes fortified with NADPH, the rate of oxidative metabolism of Compound A was 0.3, 0.05, 0.07, and 0.21 mmol/min/mg protein, respectively. The major metabolites in mouse, rat, and dog microsomes had molecular weights 16 (M+16) and 18 (M+18) units higher than the parent compound. In human microsomes, the major metabolite had a molecular weight 16 units higher than the parent (M+16).

(b) Liver S9 Incubations

After incubation of Compound A (10500 ng/mL; 20 μM) with mouse, rat, dog, and human liver S9 fractions, the rate of oxidative metabolism of Compound A was 0.06, 0.04, 0.03, and 0.06 mmol/min/mg protein, respectively. All species showed similar metabolic profiles with the major metabolites being M+16 and M+18.

(c) Inhibition of Human CYP Enzymes

The ability of Compound A to inhibit the major human cytochrome P450s (CYPs), responsible for the metabolism of drugs, was evaluated in vitro using recombinant human CYP isoforms. Compound A was found to be a moderately potent inhibitor of human CYP2C19 ($IC_{50}$=2.4 μM), CYP3A4 ($IC_{50}$=7.1 μM), and CYP2C9 ($IC_{50}$=10.6 μM). It showed weak interactions with CYP1A2 and CYP2D6 ($IC_{50}$>70 μM). The in vitro $IC_{50}$ values for CYP2C19, CYP3A4, and CYP2C9 suggest that this compound may have the potential to alter the metabolic clearance of drugs that are highly metabolized by CYP2C19, CYP3A4, and CYP2C9, and is unlikely to significantly alter the metabolic clearance of drugs metabolized by CYP1A2 and CYP2D6.

(d) Metabolism by Specific CYP Enzymes

Compound A was incubated with human liver microsomes along with compounds specific for the inhibition of individual cytochrome P450s commonly involved in drug metabolism. The inhibitors used were; furafylline (CYP1A2), sulfaphenazole (CYP2C9), tranylcypromine (CYP2C19), quinidine (CYP2D6), troleandomycin (CYP3A4), and ketoconazole (CYP3A4). Significant inhibition was observed only with the CYP3A4 inhibitors, both of which completely inhibited the biotransformation of Compound A. Thus, in humans, Compound A may be a substrate for CYP3A4.

Example 25

Pharmacokinetics: In Vivo Metabolism Studies

The metabolism of Compound A was investigated in rats following IV (2 mg/kg) and oral (8 mg/kg) administration.

Urine was collected over a 24 hour period. Another study was conducted in bile-duct cannulated (BDC) rats where bile was collected over a 9 hour period after IV (2 mg/kg) and oral (8 mg/kg) administration of Compound A. Samples were analyzed for parent compound by LC/MS/MS assay, and for exploratory metabolite elucidation. No drug related material was detected in the bile over 9-h postdose period. The percent of the dose recovered in the urine within 24 h, as Compound A, accounted for approximately 18% and 2.4% after IV and oral administration, respectively. No other drug related peaks were detected in the urine. The low recovery of Compound A is presumably related to collection of urine over a limited period of 24 h postdose. Furthermore, it should be noted that the stability of Compound A in rat urine is not known.

Example 26

Pharmacodynamic Studies

The minimum effective dose of Compound A, given as a constant rate 10-h IV infusion, was determined in mice bearing subcutaneous Pat-7 tumors. Single doses of Compound A (2, 4, 8, and 16 mg/kg) were given via IV infusion. Tumor growth delay, equivalent to log cell kill values of 0.1 (P=0.79, not significant), 0.7 (P=0.019, significant), 1.1 (P=0.004, significant), and 1.7 (P=0.001, significant) were observed for the 2, 4, 8, and 16 mg/kg doses, respectively. Hence it appears that the minimum effective dose for Compound A, given as a 10-h IV infusion, is between 2 and 4 mg/kg. The apparent steady-state concentrations of Compound A at doses of 2 and 4 mg/kg were approximately in the range of 18–31 ng/mL (35–60 nM).

Example 27

Synthesis of Compound A

Method for the synthesis of Compound A is described in U.S. Pat. No. 6,262,094, issued Jul. 17, 2001, the entire contents of which are herein incorporated by reference.
Conversion of Epothilone B to Epothilone F

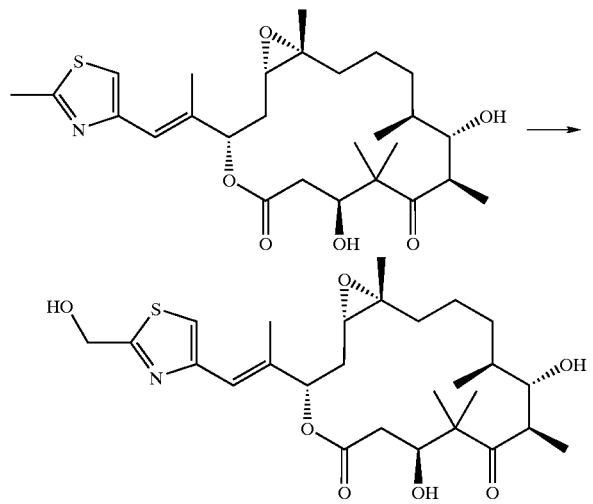

(i) 1.98 g (3.90 mmol) of Epothilone B was placed under Argon and dissolved in 60 mL dry $CH_2Cl_2$. To this solution was added 0.720 g mCPBA (4.17 mmol, 1.07 equivalents). The mixture was allowed to stir at 25° C. for 5.5 hours. The reaction mixture was quenched with 60 mL $NaHCO_3$, and extracted with 3×75 mL of $CHCl_3$. The organic phase was washed with 100 mL water followed by 70 mL of 5% $Na_2SO_{3(aq)}$ and then 70 mL brine. The organic phase was then dried over $Na_2SO_4$. The crude reaction product was chromatographed using silica gel eluting with 2% MeOH in $CHCl_3$ to yield 0.976 g of the N-oxide (48%) as a white fluffy solid.

(ii) To a resealable tube under Argon was added 0.976 g of the N-oxide (1.86 mmol) dissolved in 35 mL dry $CH_2Cl_2$, 2,6-lutidine (1.73 mL, 14.88 mmol, 8 equivalents) and $(CF_3CO)_2O$ (1.84 mL, 13.02 mmol, 7 equivalents). The tube was sealed and heated at 70° C. for 25 min. The mixture was allowed to cool and the solvent was removed under a stream of argon, followed by concentration to a few mL of dark yellow solution under vacuum. The reaction was diluted with 25 mL MeOH and 2.9 mL of 28% $NH_4OH_{(aq)}$ was added. The mixture was heated to 45° C. for 20 min, then cooled to room temperature. The crude product was concentrated on the rotary evaporator and chromatographed using silica gel eluting with 4% MeOH in $CHCl_3$ to yield 0.815 g of Epothilone F (84%).

Synthesis of 21-azido-epothilones

Example: [1S-[1R*,3R*(E),7R*,10S*,11R*,12R*, 16S*]]-3-[2-[2-(Azidomethyl)-4-thiazolyl]-1-methylethenyl]-7,11-dihydroxy-8,8,10,12,16-pentamethyl-4,17-dioxabicyclo[14.1.0]heptadecane-5,9-dione.

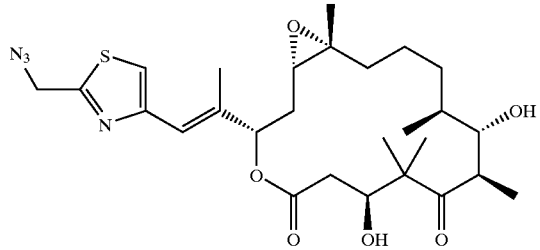

To a stirred solution of epothilone F from Example 1 above (957 mg, 1.83 mmol) in 20.0 mL tetrahydrofuran at 0° C. under Argon was added 0.47 mL diphenylphosphoryl azide (604 mg, 2.19 mmol, 1.2 equivalents). The mixture was stirred for approximately 3 min. 1,8-diazabicyclo[5.4.0]undec-7-ene (0.27 mL, 278 mg, 1.83 mmol, 1 equivalents) was then added and the mixture was stirred at 0° C. After 2 hours, the mixture was warmed to 25° C. and stirred for 20 hours. The reaction mixture was diluted with 150 mL ethyl acetate and washed with 50 mL $H_2O$. The aqueous layer was extracted with 35 mL ethyl acetate. The combined organic layers were dried over $Na_2SO_4$ and concentrated under vacuum. The crude material was chromatographed using silica gel eluted with 50% ethyl acetate in hexanes to afford 913 mg (91%) of 21-azido-epothilone B, as a clear, colorless oil. MS (ESI$^+$): 549.3 (M+H)$^+$; $^1$H-NMR (300 MHz, $CDCl_3$); δ=6.59 (bs, 17-H), 7.04 (s, 19-H), 4.63 (s, 21-$H_2$); HRMS (DCI); $C_{27}H_{40}N_4O_6S$: [M$^+$] calculated 549.2747, found 549.2768.

Synthesis of 21-amino-epothilones

Example: [1S-[1R*,3R*(E),7R*,10S*,11 R*,12R*, 16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione.

Lindlar catalyst, 18.0 mg, was suspended in 500 μL of ethanol in an $H_2$ atmosphere and was saturated. Then, 15.9 mg (29.0 μmol) of 21-azido-epothilone B from Example 2 above, dissolved in an ethanol-methanol mixture, was added. After stirring for 30 minutes at room temperature, the suspension is filtered through Celite, and washed with ethyl acetate. The solvent was removed from the organic phase and dried in high vacuum. The purification of the crude product was done through PSC (solvent: $CH_2Cl_2$/methanol 90:10), whereupon 12.3 mg (81%) of 21-amino-epothilone B and 1 mg (6%) of educt is obtained.

$^1$H-NMR (300 MHz, $CDCl_3$); δ=6.58 (bs, 17-H), 7.05 (s, 19-H), 4.15 (s, 21-$H_2$); HRMS (DCI); $C_{27}H_{42}N_2O_6S$: [M+H$^+$] calculated 522.2764, found 522.2772.

Synthesis of 21-amino-epothilones (Alternative)
[1S-[1R*,3R*(E),7R*,10S*,11R*,12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione

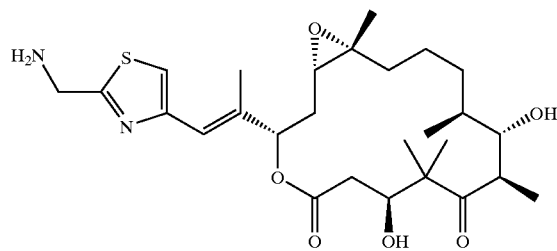

To a stirred solution of 21-azido-epothilone B (Example 2) (1.070 g, 1.950 mmol) in 30.0 mL tetrahydrofuran under Argon was added 0.22 mL of trimethylphosphine (0.163 g, 2.145 mmol, 1.1 equivalents). $H_2O$ (5.5 mL) was then added, and the mixture was allowed to stir at 25° C. After 3 hours, the azide was completely consumed and 3 mL of 28% aqueous $NH_4OH_{(aq)}$ was added to complete the conversion of phosphoryl imine to amine. After stirring at 25° C. for 1 hour the solvents were removed under vacuum. The crude material was chromatographed using silica gel eluted with 1% $Et_3N$, 2.5% MeOH in $CHCl_3$ to yield 924 mg (91%) of 21-amino-epothilone B, as a white solid. MS (ESI$^+$): 523.3 (M+H)$^+$ Example 28

Compound A Formulation

Compound A was dissolved in 1280 mL of an aqueous solution of citrate buffer and dextran 40 which had been pre-cooled to 5° C. Once the drug powder had become completely dissolved, the solution pH was adjusted and the batch manufacture was completed by the addition of 178 mL of Water for Injection.

The solution formed above was promptly lyophilized in a Virtis Genesis lyophilizer at −15° C. under light protectant conditions over a period of 34 hours. The resultant lyophile was then further dried at 25° C. under high vacuum for 24 hours. No detectable degradation of the drug was observed during these procedures. The lyophile was packaged under sterile conditions into 15 mL vials, each containing 10 mg of drug plus standard excess to allow for vial/needle/syringe loss.

The lyophile was reconstituted with 5.4 mL of Sterile Water for Injection, USP, to achieve a final drug concentration of 2 mg/ml. Once dissolution was effected by gently swirling the vial, the resultant solution was diluted to achieve a concentration of 0.1 mg/mL by the addition of 20 mL of 0.9% Sodium Chloride Injection per mL of constituted drug product.

Example 29

Lyophilized Formulation of Compound A

1. Stability

Initially, determination of the effect of various buffers and bulking agents on solution and lyophile stability of the Compound A formulation was performed. For the lyophilized product, the goal was to minimize free water available to Compound A by selecting excipients that would facilitate the diffusive loss of water from the lyophile by rendering the cake porous or by using excipients that would be sufficiently hygroscopic to absorb the residual moisture away from the active compound. The buffer was used to maintain a pH of about 6. The buffers evaluated include bicarbonate, citrate and succinate and the bulking agents evaluated include mannitol, dextran 40, histidine, lysine and sodium chloride. Stability data for some of these lyophilized prototype formulations are presented in Table 5. Based on the results of these stability studies, a citrate buffered formulation containing dextran 40 was preferable.

TABLE 5

Stability of Lyophilized Compound A Formulation

| Temp (° C.) | Weeks | Formulation: Drug Alone | | Formulation: Drug plus Dextran 40 | | Formulation: Drug plus Dextran 40 plus Citrate Buffer | |
|---|---|---|---|---|---|---|---|
| | | Percent of Initial Potency Remaining | Total Impurity Index | Percent of Initial Potency Remaining | Total Impurity Index | Percent of Initial Potency Remaining | Total Impurity Index |
| | 0 | 100.0 | 0.68 | 100.0 | 0.75 | 100.0 | 0.51 |
| 5 | 2 | 99.3 | 0.85 | 100.2 | 0.99 | 100.1 | 0.64 |
| | 4 | 99.7 | 0.86 | 100.2 | 0.62 | 100.0 | 0.37 |
| 25 | 2 | 97.2 | 1.61 | 98.8 | 1.22 | 99.6 | 0.77 |
| | 4 | 97.6 | 2.65 | 99.2 | 1.40 | 99.7 | 0.80 |
| 40 | 2 | 91.1 | 6.53 | 94.3 | 4.75 | 97.2 | 1.87 |
| | 4 | 90.7 | 7.47 | 90.4 | 7.86 | 95.8 | 2.33 |

TABLE 5-continued

Stability of Lyophilized Compound A Formulation

| Temp (° C.) | Weeks | Formulation: Drug plus Mannitol | | Formulation: Drug plus Sodium Succinate | | Formulation: Drug plus L-Lysine | |
|---|---|---|---|---|---|---|---|
| | | Percent of Initial Potency Remaining | Total Impurity Index | Percent of Initial Potency Remaining | Total Impurity Index | Percent of Initial Potency Remaining | Total Impurity Index |
| | 0 | 100.0 | 2.68 | 100.0 | 1.74 | 100.0 | 2.71 |
| 25 | 2 | 98.5 | 4.61 | 104.8 | 3.10 | 104.5 | 3.07 |
| 50 | 2 | 55.2 | 43.0 | 81.9 | 20.2 | 81.9 | 22.4 |

2. Composition of Formulation

Compound A formulation, 10 mg/vial, is a sterile, non-pyrogenic lyophilized product which appears as a white to off-white, whole or fragmented cake. In addition to the active ingredient, the lyophilized drug product contains 13.9 mg of citric acid and 110 mg of dextran 40 per vial. The pH of the bulk solution was adjusted with sodium hydroxide and/or hydrochloric acid to pH 6.0, prior to lyophilization. The quantitative composition for the formulation is presented in Table 6. A sufficient excess of drug was provided in each vial to allow for withdrawal losses. The drug product was packaged in Type I glass vials, stoppered with 20 mm closures and sealed with aluminum seals.

TABLE 6

Quantitative Composition of Compound A Formulation

| Ingredient | Ingredient Code | Amount per mL | Amount per Vial |
|---|---|---|---|
| BMS-310705-01 | N/A | 5.0 mg | 11.0 mg (1) |
| Dextran 40 USP | RM2002 | 50.0 mg | 110 mg |
| Citric Acid USP | 30061 | 6.3 mg | 13.9 mg |
| Sodium Hydroxide NF/Hydrochloric Acid NF | 40230/ 10704 | qs ad pH 6.0 | qs ad pH 6.0 |
| Water for Injection USP | 20445 | qs ad 1.0 mL | qs ad 2.20 mL (2) |

(1) At 100% purity and includes a 10% overfill for VNS losses.
(2) Removed during lyophilization.

3. Longer Term Stability of Compound A Formulation

Compound A formulation, 10 mg/vial was manufactured and placed on stability at 5° C., 25° C. and 40° C. The package components used for this batch, 15-mL Type I glass vials and 20-mm bromobutyl Omniflex® coated stoppers, were also used to package the clinical material. Stability data for samples of drug product stored at various temperature conditions for six months are presented in Table 7. During the six months of storage, there were no changes in lyophile appearance for any of the samples and there were no changes in the appearance or pH of solution from constituted lyophile samples. The data in Table 7 show that there were no changes in Compound A potency or total impurities for samples stored at 5° C. At 25° C. and 40° C., however, there were potency losses of 3% and 10%, respectively, and these losses in potency were accompanied by increases in total impurities. Stability data also showed that the drug product was sensitive to light exposure. Based on these stability results, Compound A formulation should be stored at 2° C. to 8° C., protected from light.

TABLE 7

Longer Term Stability of Compound A Formulation

| Temp. (° C.) | Time (Months) | Lyophile[1] and Constituted Solution[2] Appearance | Potency (mg/vial) | % of Initial Potency | pH | KF (% w/w) | Const. Time (min.) | Total Impurities (%) | HIAC (Counts per Vial) | |
|---|---|---|---|---|---|---|---|---|---|---|
| | | | | | | | | | ≥10μ | ≥25μ |
| | 0 | Complies | 10.76 | 100.0 | 6.09 | 1.62 | 0.5 | 0.47 | 301 | 22 |
| 5 | 1 | Complies | 10.38 | 96.5 | 6.04 | 1.82 | 0.5 | 0.37 | 233 | 14 |
| | 3 | Complies | 10.8 | 100.4 | 6.16 | 1.36 | 0.5 | 0.37 | 266 | 14 |
| | 6 | Complies | 10.68 | 99.3 | 6.17 | 1.32 | 0.5 | 0.41 | 206 | 12 |
| 25 | 0.5 | Complies | 10.74 | 99.8 | 6.11 | 1.74 | 0.5 | 0.55 | 234 | 10 |
| | 1 | Complies | 10.18 | 94.6 | 6.05 | 1.58 | 0.5 | 0.70 | 236 | 14 |
| | 3 | Complies | 10.6 | 98.5 | 6.17 | 1.42 | 0.5 | 1.21 | 568 | 33 |
| | 6 | Complies | 10.41 | 96.7 | 6.14 | 1.58 | 0.5 | 1.18 | 1250 | 36 |
| 40 | 1 | Complies | 10.12 | 94.1 | 6.02 | 2.39 | 0.5 | 2.05 | 3841 | 103 |
| | 3 | Complies | 10.1 | 93.9 | 6.16 | 1.29 | 0.5 | 4.34 | 92557 | 3344 |
| | 6 | Complies | 9.69 | 90.1 | 6.09 | 1.47 | 0.5 | 4.71 | 4943 | 131 |

[1]Lyophile appearance is white to off-white, whole or fragmented cake.
[2]Constituted solution appearance is clear, colorless solution, essentially free of particulate matter by visual inspection.

4. Reconstitution

Compound A formulation, 10 mg/vial, is constituted with Sterile Water for Injection, USP (SWFI), prior to use. The drug product was constituted by slowly injecting 5.4 mL of SWFI into the vial of BMS-310705-01 for Injection, 10 mg/vial. The vial was gently swirled until the lyophile was completely dissolved. When the lyophile was completely dissolved, the vial contained 5.5 mL of solution with a Compound A concentration of 2 mg/mL. This solution, resulting from constitution of the lyophile, must be further diluted with 0.9% Sodium Chloride Injection, USP to a final Compound A concentration ranging from 0.05 mg/mL to 0.5 mg/mL prior to administration to the patient. The infusion is to be administered through a 5 micron in-line filter extension set (B. Braun Medical Inc., Product Code FE-5010Y) and must be completed within 24 hours of lyophile constitution.

5. Storage of Compound A Formulation

Compound A formulation should be stored refrigerated (2° to 8° C.) and protected from light prior to use. After initial constitution with Sterile Water for Injection, USP, the constituted product may be stored in the vial at 5° C. or at room temperature and room light for a maximum of 24 hours. In addition, after final dilution with 0.9% Sodium Chloride Injection, USP, solutions of Compound A are stable when stored at 5° C. or at room temperature and room light for a maximum of 24 hours. Following constitution of the lyophilized drug product, all constituted and/or diluted solutions must be used within 24 hours.

The embodiments of the present invention described above are intended to be merely exemplary, and those skilled in the art will recognize, or will be able to ascertain using no more than routine experimentation, numerous equivalents of specific compounds, materials, and procedures. All such equivalents are considered to be within the scope of this invention and are encompassed by the appended claims.

What is claimed is:

1. A method of administering a compound comprising:

orally administering to a human one or more compounds of Formula I:

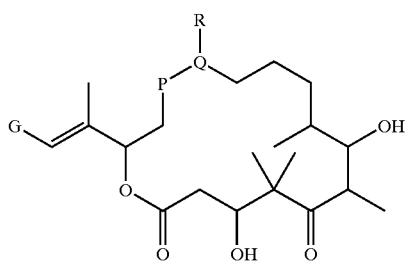

wherein:

P-Q is a C, C double bond or an epoxide;

G is

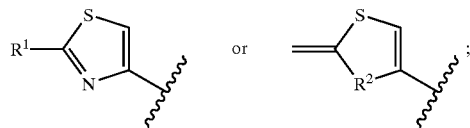

R is selected from the group consisting of H, alkyl, and substituted alkyl;

$R^1$ is selected from the group consisting of

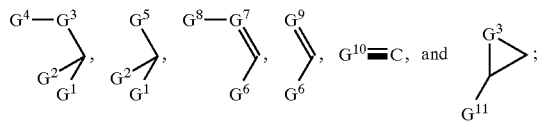

$R^2$ is

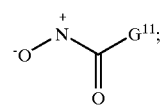

$G^1$ is selected from the group consisting of H, halogen, CN, alkyl and substituted alkyl;

$G^2$ is selected from the group consisting of H, alkyl, and substituted alkyl;

$G^3$ is selected from the group consisting of O, S, and $NZ^1$;

$G^4$ is selected from the group consisting of H, alkyl, substituted alkyl, $OZ^2$, $NZ^2Z^3$, $Z^2C=O$, $Z^4SO_2$, and optionally substituted glycosyl;

$G^5$ is selected from the group consisting of halogen, $N_3$, NCS, SH, CN, NC, $N(Z^1)_3^+$, and heteroaryl;

$G^6$ is selected from the group consisting of H, alkyl, substituted alkyl, $CF_3$, $OZ^5$, $SZ^5$, and $NZ^5Z^6$;

$G^7$ is $CZ^7$ or N;

$G^8$ is selected from the group consisting of H, halogen, alkyl, substituted alkyl, $OZ^{10}$, $SZ^{10}$, $NZ^{10}Z^{11}$;

$G^9$ is selected from the group consisting of O, S, —NH—NH—, and —N=N—;

$G^{10}$ is N or $CZ^{12}$;

$G^{11}$ is selected from the group consisting of $H_2N$, substituted $H_2N$, alkyl, substituted alkyl, aryl, and substituted aryl;

$Z^1$, $Z^6$, $Z^9$, and $Z^{11}$ are independently selected from the group consisting of H, alkyl, substituted alkyl, acyl, and substituted acyl;

$Z^2$ is selected from the group consisting of H, alkyl, substituted alkyl, aryl, substituted aryl, and heterocycle;

$Z^3$, $Z^5$, $Z^8$, and $Z^{10}$ are independently selected from the group consisting of H, alkyl, substituted alkyl, acyl, substituted acyl, aryl, and substituted aryl;

$Z^4$ is selected from the group consisting of alkyl, substituted alkyl, aryl, substituted aryl, and heterocycle;

$Z^7$ is selected from the group consisting of H, halogen, alkyl, substituted alkyl, aryl, substituted aryl, $OZ^8$, $SZ^8$, and $NZ^8Z^9$; and $Z^{12}$ is selected from the group consisting of H, halogen, alkyl, substituted alkyl, aryl, and substituted aryl;

with the proviso that when $R^1$ is

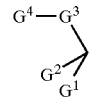

$G^1$, $G^2$, $G^3$, and $G^4$ cannot simultaneously have the following meanings:

$G^1$ and $G^2$=H, $G^3$=O and $G^4$=H or $Z^2C$=O where $Z^2$=alkyl, and with the proviso that when $R^1$ is

$G^1$, $G^2$ or $G^5$ cannot simultaneously have the following meanings: $G^1$ and $G^2$=H, and $G^5$=F;

or a pharmaceutically acceptable salt, solvate, clathrate, hydrate or prodrug thereof; and orally administering one or more pharmaceutically acceptable acid neutralizing buffers in an amount sufficient to reduce decomposition of said one or more compounds, or said pharmaceutically acceptable salt, solvate, clathrate, hydrate, or prodrug thereof.

2. The method of claim 1 wherein said compound is

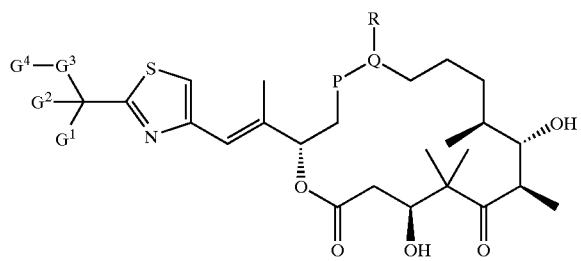

Ia wherein:

P-Q is a C,C double bond or an epoxide;

R is H or a methyl;

$G^1$ is selected from the group consisting of H, alkyl, a substituted alkyl, and halogen;

$G^2$ is selected from the group consisting of H, alkyl, and substituted alkyl;

$G^3$ is selected from the group consisting of O, S, and $NZ^1$;

$G^4$ is selected from the group consisting of H, alkyl, substituted alkyl, $OZ^2$, $NZ^2Z^3$, $Z^2C$=O, $Z^4SO_2$, and an optionally substituted glycosyl;

$Z^1$ is selected from the group consisting of H, alkyl, substituted alkyl, acyl, and substituted acyl;

$Z^2$ is selected from the group consisting of H, alkyl, substituted alkyl, aryl, substituted aryl, and heterocycle;

$Z^3$ is selected from the group consisting of H, alkyl, substituted alkyl, acyl, and substituted acyl; and $Z^4$ is selected from the group consisting of alkyl, substituted alkyl, aryl, substituted aryl, and heterocycle;

with the proviso that $G^1$, $G^2$, $G^3$, and $G^4$ cannot have simultaneously the following meanings: $G^1$ and $G^2$=H, $G^3$=O, and $G^4$=H or $Z^2C$=O with $Z^2$=alkyl.

3. The method of claim 2 wherein said compound is

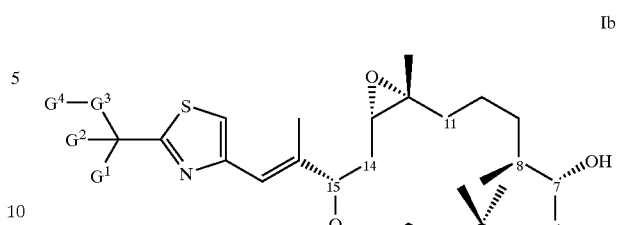

Ib wherein $G^1$, $G^2$, $G^3$, $G^4$, $Z^1$, $Z^2$, and $Z^3$ are as defined in claim 2.

4. The method of claim 3 wherein said compound is [1S-[1R*,3R*(E),7R*, 10S*,11R*,12R*,16S*]]-3-[2-[2 (aminomethyl)-4-thiazolyl]-1-methylethenyl]-7,11-dihydroxy-8,8,10,12,16-pentamethyl-4,17-dioxabicyclo 14.1.0]heptadecane-5,9-dione.

5. The method of claim 1 wherein said pharmaceutically acceptable acid neutralizing buffer is administered concurrently with said compound.

6. The method of claim 1 wherein said pharmaceutically acceptable acid neutralizing buffer is administered before said compound.

7. The method of claim 6 wherein said pharmaceutically acceptable acid neutralizing buffer is administered not more than about 1 hour before said compound.

8. The method of claim 1 wherein said pharmaceutically acceptable acid neutralizing buffer is administered after said compound.

9. The method of claim 8 wherein said pharmaceutically acceptable acid neutralizing buffer is administered nor more than about 1 hour after said compound.

10. The method of claim 1 wherein said pharmaceutically acceptable acid neutralizing buffer is administered before and after said compound.

11. The method of claim 10 wherein said pharmaceutically acceptable acid neutralizing buffer is administered not more than about 1 hour before and not more than about 1 hour after said compound is administered.

12. The method of claim 1 wherein said pharmaceutically acceptable acid neutralizing buffer is administered in an amount sufficient to deliver at least about 20 milliequivalents of acid neutralization capacity.

13. The method of claim 1 wherein said pharmaceutically acceptable acid neutralizing buffer is administered in an amount sufficient to deliver at least about 30 milliequivalents of acid neutralization capacity.

14. The method of claim 1 wherein said pharmaceutically acceptable acid neutralizing buffer is administered in an amount sufficient to deliver at least about 40 milliequivalents of acid neutralization capacity.

15. The method of claim 1 wherein said pharmaceutically acceptable acid neutralizing buffer is administered as an aqueous solution having a pH of between about 5 to 9.

16. The method of claim 1 wherein said pharmaceutically acceptable acid neutralizing buffer is administered as an aqueous solution having a pH of between about 6 to 8.5.

17. The method of claim 1 wherein said pharmaceutically acceptable acid neutralizing buffer is administered as an aqueous solution having a pH of between about 7 to 8.

18. The method of claim 1 wherein said compound is administered every 3 days to 7 days, followed by a period of 1 week to 3 weeks where there is no treatment.

19. The method of claim 18 wherein said compound is administered every 3 days, followed by a period of 1 week where there is no treatment.

20. The method of claim 18 wherein said compound is administered every 5 days, followed by a period of 1 week where there is no treatment.

21. The method of claim 18 wherein said compound is administered every 7 days, followed by a period of 1 week where there is no treatment.

22. The method of claim 1 wherein said pharmaceutically acceptable acid neutralizing buffer is administered as an aqueous solution comprising anhydrous dibasic sodium phosphate, sodium citrate dihydrate, and anhydrous citric acid.

23. The method of claim 22 wherein the pH of said aqueous solution is about 7.

24. The method of claim 1 wherein the bioavailability of said one or more compounds or sida pharmaceutically acceptable salt, solvate, clathrate, hydrate, or prodrug thereof is at least about 20 percent.

25. The method of claim 1 wherein the bioavailability of said one or more compounds or said pharmaceutically acceptable salt, solvate, clathrate, hydrate, or prodrug thereof is at least about 30 percent.

26. The method of claim 1 wherein said one or more compounds or said pharmaceutically acceptable salt, solvate, clathrate, hydrate, or prodrug thereof is orally administered as a solution in propylene glycol and ethanol, wherein the ratio of propylene glycol:ethanol is about 80:20.

27. The method of claim 26 wherein said compound is [1S-[1R*,3R*(E),7R*, 10S *,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

28. The method of claim 1 wherein said one or more compounds or said pharmaceutically acceptable salt, solvate, clathrate, hydrate, or prodrug thereof is administered in a total amount of about 0.05 to about 200 mg/kg/day.

29. The method of claim 28 wherein said one or more compounds or said pharmaceutically acceptable salt, solvate, clathrate, hydrate, or prodrug thereof is administered in about 2 to 4 divided doses.

30. The method of claim 29 wherein said compound is [1S-[1R*,3R*(E),7R*, 10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

31. The method of claim 1 wherein said pharmaceutically acceptable acid neutralizing buffer is selected from the group consisting of tartaric acid, lactic acid, succinic acid, citric acid, acetic acid, ascorbic acid, aspartic acid, glutamic acid, and salts thereof.

32. The method of claim 1 comprising:

(a) orally administering an aqueous solution of said pharmaceutically acceptable acid neutralizing buffer;

(b) orally administering said one or more compounds or said pharmaceutically acceptable salt, solvate, clathrate, hydrate, or prodrug thereof as a solution in propylene glycol; and (c) orally administering said aqueous solution of said pharmaceutically acceptable acid neutralizing buffer;

wherein said pharmaceutically acceptable acid neutralizing buffer comprises anhydrous dibasic sodium phosphate, sodium citrate dihydrate, and anhydrous citric acid.

33. A kit for use in a method of administering compounds which comprises:

(i) a first component comprising one or more compounds of Formula I:

wherein:
P-Q is a C, C double bond or an epoxide;
G is $R^1$ or $R^2$ ;

R is selected from the group consisting of H, alkyl, and substituted alkyl;
$R^1$ is selected from the group consisting of $G^4$—$G^3$, $G^5$, $G^8$—$G^7$, $G^9$, $G^3$ $G^2$, $G^2$, , , $G^{10}$=C, and $G^{11}$ ;
$G^1$, $G^1$, $G^6$, $G^6$, $R^2$ is $G^{11}$ ;

$G^1$ is selected from the group consisting of H, halogen, CN, alkyl, and substituted alkyl;
$G^2$ is selected from the group consisting of H, alkyl, and substituted alkyl;
$G^3$ is selected from the group consisting of O, S, and $NZ^1$;
$G^4$ is selected from the group consisting of H, alkyl, substituted alkyl, $OZ^2$, $NZ^2Z^3$, $Z^2C$=O, $Z^4SO_2$, and optionally substituted glycosyl;
$G^5$ is selected from the group consisting of halogen, $N_3$, NCS, SH, CN, NC, $N(Z^1)_3^+$, and heteroaryl;
$G^6$ is selected from the group consisting of H, alkyl, substituted alkyl, $CF_3$, $OZ^5$, $SZ^5$, and $NZ^5Z^6$;
$G^7$ is $CZ^7$ or N;
$G^8$ is selected from the group consisting of H, halogen, alkyl, substituted alkyl, $OZ^{10}$, $SZ^{10}$, and $NZ^{10}Z^{11}$;
$G^9$ is selected from the group consisting of O, S, —NH—NH—, and —N=N—;
$G^{10}$ is N or $CZ^{12}$;
$G^{11}$ is selected from the group consisting of $H_2N$, substituted $H_2N$, alkyl, substituted alkyl, aryl, and substituted aryl;
$Z^1$, $Z^6$, $Z^9$, and $Z^{11}$ are independently selected from the group consisting of H, alkyl, substituted alkyl, acyl, and substituted acyl;
$Z^2$ is selected from the group consisting of H, alkyl, substituted alkyl, aryl, substituted aryl, and heterocycle;

$Z^3$, $Z^5$, $Z^8$, and $Z^{10}$ are independently selected from the group consisting of H, alkyl, substituted alkyl, acyl, substituted acyl, aryl, and substituted aryl;

$Z^4$ is selected from the group consisting of alkyl, substituted alkyl, aryl, substituted aryl, and heterocycle;

$Z^7$ is selected from the group consisting of H, halogen, alkyl, substituted alkyl, aryl, substituted aryl, $OZ^8$, $SZ^8$, and $NZ^8Z^9$; and $Z^{12}$ is selected from the group consisting of H, halogen, alkyl, substituted alkyl, aryl, and substituted aryl;

with the proviso that when $R^1$ is

$G^1$, $G^2$, $G^3$, and $G^4$ cannot simultaneously have the following meanings:

$G^1$ and $G^2$=H, $G^3$=O, and $G^4$=H or $Z^2$C=O where $Z^2$=alkyl, and with the proviso that when $R^1$ is

$G^1$, $G^2$ or $G^5$ cannot simultaneously have the following meanings: $G^1$ and $G^2$=H, and $G^5$=F; or a pharmaceutically acceptable salt, solvate, clathrate, hydrate, or prodrug thereof; and (ii) a second component comprising a pharmaceutically acceptable acid neutralizing buffer, wherein said first component and said second component are provided as an oral dosage form or as a pharmaceutical composition that can be reconstituted with a solvent to provide a liquid oral dosage.

34. The kit of claim 33 wherein at least one of said first component or said second component is anhydrous.

35. The kit of claim 33 wherein at least one of said first component or said second component is provided as said pharmaceutical composition that can be reconstituted with a solvent to provide a liquid oral dosage form.

36. The kit of claim 35 wherein at least one of said first component or said second component is provided as a tablet.

37. The kit of claim 35 wherein at least one of said first component or said second component is anhydrous.

38. The kit of claim 35 further comprising solvents for reconstituting said first or second components.

39. The kit of claim 38 wherein said solvent for reconstituting said first component is a mixture of propylene glycol and ethanol.

40. The kit of claim 33 wherein said first component and said second component are provided as a liquid oral dosage form.

41. The kit of claim 40 wherein said one or more compounds or said pharmaceutically acceptable salt, solvate, clathrate, hydrate, or prodrug thereof is present in an amount of between about 0.05 and about 200 mg; and said pharmaceutically acceptable acid neutralizing buffer is present in an amount sufficient to provide at least about 20 milliequivalents of acid neutralization capacity.

42. The kit of claim 33 wherein said first component and said second component are provided as a pharmaceutical composition that can be reconstituted with a solvent to provide said liquid oral dosage form; wherein said one or more compounds or said pharmaceutically acceptable salt, solvate, clathrate, hydrate, or prodrug thereof is present in an amount of between about 0.05 and about 200 mg; and said pharmaceutically acceptable acid neutralizing buffer is present in an amount sufficient to provide at least about 20 milliequivalents of acid neutralization capacity.

43. The kit of claim 33 wherein said compound is [1S-[1R*,3R*(E),7R*, 10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione and said pharmaceutically acceptable acid neutralizing buffer comprises dibasic sodium phosphate, sodium citrate, and anhydrous citric acid.

44. A pharmaceutical composition suitable for oral administration to a mammal comprising:

(i) one or more compounds of Formula I:

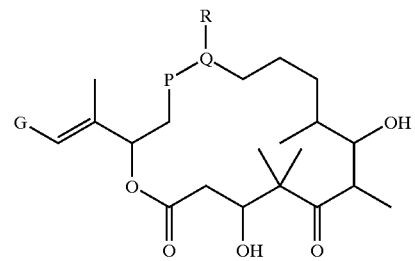

wherein:
P-Q is a C, C double bond or an epoxide;
G is

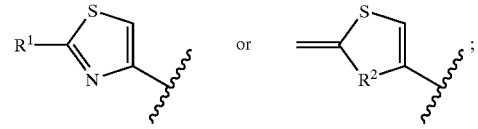

R is selected from the group consisting of H, alkyl, and substituted alkyl;

$R^1$ is selected from the group consisting of

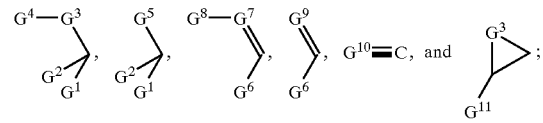

$R^2$ is

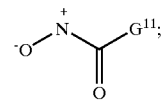

$G^1$ is selected from the group consisting of H, halogen, CN, alkyl, and substituted alkyl;

$G^2$ is selected from the group consisting of H, alkyl, and substituted alkyl;

$G^3$ is selected from the group consisting of O, S, and $NZ^1$;

$G^4$ is selected from the group consisting of H, alkyl, substituted alkyl, $OZ^2$, $NZ^2Z^3$, $Z^2$C=O, $Z^4SO_2$, and optionally substituted glycosyl;

$G^5$ is selected from the group consisting of halogen, $N_3$, NCS, SH, CN, NC, $N(Z^1)_3{}^+$, and heteroaryl;

$G^6$ is selected from the group consisting of H, alkyl, substituted alkyl, $CF_3$, $OZ^5$, $SZ^5$, and $NZ^5Z^6$;

$G^7$ is $CZ^7$ or N;

$G^8$ is selected from the group consisting of H, halogen, alkyl, substituted alkyl, $OZ^{10}$, $SZ^{10}$, and $NZ^{10}Z^{11}$;

$G^9$ is selected from the group consisting of O, S, —NH—NH—, and —N=N—;

$G^{10}$ is N or $CZ^{12}$;

$G^{11}$ is selected from the group consisting of $H_2N$, substituted $H_2N$, alkyl, substituted alkyl, aryl, and substituted aryl;

$Z^1$, $Z^6$, $Z^9$, and $Z^{11}$ are independently selected from the group consisting of H, alkyl, substituted alkyl, acyl, and substituted acyl;

$Z^2$ is selected from the group consisting of H, alkyl, substituted alkyl, aryl, substituted aryl, and heterocycle;

$Z^3$, $Z^5$, $Z^8$, and $Z^{10}$ are independently selected from the group consisting of H, alkyl, substituted alkyl, acyl, substituted acyl, aryl, and substituted aryl;

$Z^4$ is selected from the group consisting of alkyl, substituted alkyl, aryl, substituted aryl, and heterocycle;

$Z^7$ is selected from the group consisting of H, halogen, alkyl, substituted alkyl, aryl, substituted aryl, $OZ^8$, $SZ^8$, and $NZ^8Z^9$; and $Z^{12}$ is selected from the group consisting of H, halogen, alkyl, substituted alkyl, aryl, and substituted aryl;

with the proviso that when $R^1$ is

$G^1$, $G^2$, $G^3$, and $G^4$ cannot simultaneously have the following meanings:

$G^1$ and $G^2$=H, $G^3$=O, and $G^4$=H or $Z^2C$=O where $Z^2$=alkyl, and with the proviso that when $R^1$ is

$G^1$, $G^2$, or $G^5$ cannot simultaneously have the following meanings: $G^1$ and $G^2$=H, and $G^5$=F;

or a pharmaceutically acceptable salt, solvate, clathrate, hydrate, or prodrug thereof, in solid form; and (ii) a solid pharmaceutically acceptable acid neutralizing buffer in an amount sufficient to reduce decomposition of said one or more compounds, or said pharmaceutically acceptable salt, solvate, clathrate, hydrate, or prodrug thereof when said pharmaceutical composition is reconstituted with a solvent to provide a liquid oral dosage form.

45. The pharmaceutical composition of claim 44 wherein said pharmaceutically acceptable acid neutralizing buffer provides said liquid oral dosage form having a pH between about 5 to 9.

46. The pharmaceutical composition of claim 44 wherein said pharmaceutically acceptable acid neutralizing buffer is present in an amount sufficient to provide at least about 20 milliequivalents of acid neutralization capacity.

47. The pharmaceutical composition of claim 44 wherein said pharmaceutically acceptable acid neutralizing buffer is a dibasic phosphate-citric acid-citrate buffer.

48. The pharmaceutical composition of claim 44 wherein said one or more compounds or said pharmaceutically acceptable salt, solvate, clathrate, hydrate, or prodrug thereof is present in an amount of between about 0.05 and about 200 mg.

49. The pharmaceutical composition of claim 44 wherein said compound is [1S-[1R*,3R*(E),7R*,10S*,11R*,12R,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

50. A kit comprising said pharmaceutical composition of claim 44 and a solvent for reconstituting said pharmaceutical composition to provide an oral dosage form.

51. The kit of claim 50 wherein said solvent comprises propylene glycol, ethanol, and phosphate buffer (1M, pH 8).

52. The kit of claim 51 wherein said ratio of propylene glycol:ethanol:phosphate buffer is about 58:12:30.

53. A liquid oral dosage form suitable for oral administration to a mammal comprising:

(i) one or more compounds of Formula I:

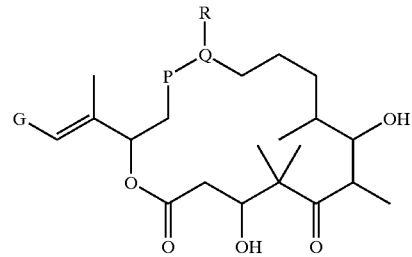

wherein:

P-Q is a C, C double bond or an epoxide;

G is

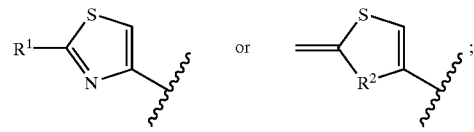

R is selected from the group consisting of H, alkyl, and substituted alkyl;

$R^1$ is selected from the group consisting of

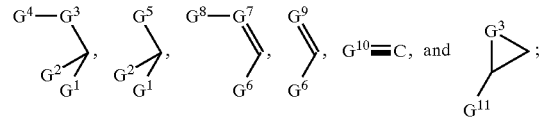

$R^2$ is

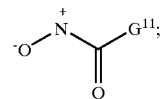

$G^1$ is selected from the group consisting of H, halogen, CN, alkyl, and substituted alkyl;

$G^2$ is selected from the group consisting of H, alkyl, and substituted alkyl;

$G^3$ is selected from the group consisting of O, S, and $NZ^1$;

$G^4$ is selected from the group consisting of H, alkyl, substituted alkyl, $OZ^2$, $NZ^2Z^3$, $Z^2C$=O, $Z^4SO_2$, and optionally substituted glycosyl;

G⁵ is selected from the group consisting of halogen, N₃, NCS, SH, CN, NC, N(Z¹)₃⁺, and heteroaryl;

G⁶ is selected from the group consisting of H, alkyl, substituted alkyl, CF₃, OZ⁵, SZ⁵, and NZ⁵Z⁶;

G⁷ is CZ⁷ or N;

G⁸ is selected from the group consisting of H, halogen, alkyl, substituted alkyl, OZ¹⁰, SZ¹⁰, and NZ¹⁰Z¹¹;

G⁹ is selected from the group consisting of O, S, —NH—NH—, and —N═N—;

G¹⁰ is N or CZ¹²;

G¹¹ is selected from the group consisting of H₂N, substituted H₂N, alkyl, substituted alkyl, aryl, and substituted aryl;

Z¹, Z⁶, Z⁹, and Z¹¹ are independently selected from the group consisting of H, alkyl, substituted alkyl, acyl, and substituted acyl;

Z² is selected from the group consisting of H, alkyl, substituted alkyl, aryl, substituted aryl, and heterocycle;

Z³, Z⁵, Z⁸, and Z¹⁰ are independently selected from the group consisting of H, alkyl, substituted alkyl, acyl, substituted acyl, aryl, and substituted aryl;

Z⁴ is selected from the group consisting of alkyl, substituted alkyl, aryl, substituted aryl, and heterocycle;

Z⁷ is selected from the group consisting of H, halogen, alkyl, substituted alkyl, aryl, substituted aryl, OZ⁸, SZ⁸, and NZ⁸Z⁹; and Z¹² is selected from the group consisting of H, halogen, alkyl, substituted alkyl, aryl, and substituted aryl;

with the proviso that when R¹ is

G¹, G², G³, and G⁴ cannot simultaneously have the following meanings:

G¹ and G²=H, G³=O, and G⁴=H or Z²C═O where Z²=alkyl, and with the proviso that when R¹ is

G¹, G² or G⁵ cannot simultaneously have the following meanings: G¹ and G²=H, and G⁵=F;

or a pharmaceutically acceptable salt, solvate, clathrate, hydrate, or prodrug thereof;

(ii) a pharmaceutically acceptable liquid carrier; and (iii) a pharmaceutically acceptable acid neutralizing buffer in an amount sufficient to reduce decomposition of said one or more compounds, or said pharmaceutically acceptable salt, solvate, clathrate, hydrate, or prodrug thereof compared to a pharmaceutical composition without said buffer.

54. The liquid oral dosage form of claim 53 wherein said compound is [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

55. The liquid oral dosage form of claim 53 wherein the pH of said liquid oral dosage form is between about 5 to 9.

56. The liquid oral dosage form of claim 53 wherein said pharmaceutically acceptable acid neutralizing buffer is present in an amount sufficient to provide at least about 20 milliequivalents of acid neutralization capacity.

57. The liquid oral dosage form of claim 53 wherein said pharmaceutically acceptable acid neutralizing buffer is dibasic phosphate-citric acid-citrate buffer.

58. The liquid oral dosage form of claim 53 wherein said solvent is propylene glycol, ethanol, and water buffered with a phosphate buffer at pH about 8.

59. The liquid oral dosage form of claim 58 wherein said propylene glycol, ethanol, and water buffered with a phosphate buffer are present in a ratio of about 58:12:30.

60. The liquid oral dosage form of claim 58 wherein said compound is [1S-[1R*,3R*(E),7R*,10S*,11R*, 12R*, 16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

61. The liquid oral dosage form of claim 53 wherein said one or more compounds or said pharmaceutically acceptable salt, solvate, clathrate, hydrate, or prodrug thereof is present in an amount of between about 0.05 and about 200 mg.

62. A dispersible buffered tablet which comprises:
(i) one or more compounds of Formula I:

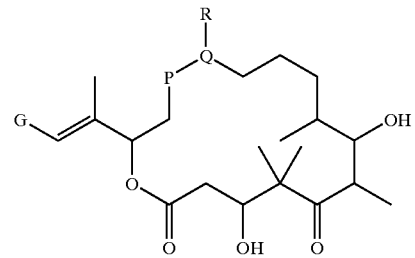

I wherein:

P-Q is a C, C double bond or an epoxide;

G is

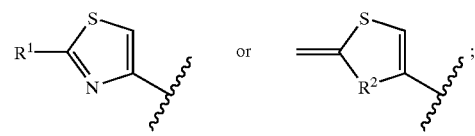

R is selected from the group consisting of H, alkyl, and substituted alkyl;

R¹ is selected from the group consisting of

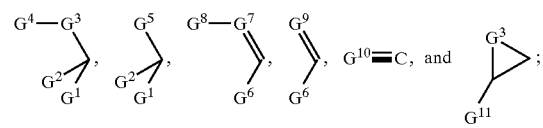

R² is

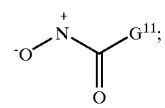

G¹ is selected from the group consisting of H, halogen, CN, alkyl, and substituted alkyl;

G² is selected from the group consisting of H, alkyl, and substituted alkyl;

$G^3$ is selected from the group consisting of O, S, and $NZ^1$;

$G^4$ is selected from the group consisting of H, alkyl, substituted alkyl, $OZ^2$, $NZ^2Z^3$, $Z^2C=O$, $Z^4SO_2$, and optionally substituted glycosyl;

$G^5$ is selected from the group consisting of halogen, $N_3$, NCS, SH, CN, NC, $N(Z^1)_3^+$, and heteroaryl;

$G^6$ is selected from the group consisting of H, alkyl, substituted alkyl, $CF_3$, $OZ^5$, $SZ^5$, and $NZ^5Z^6$;

$G^7$ is $CZ^7$ or N;

$G^8$ is selected from the group consisting of H, halogen, alkyl, substituted alkyl, $OZ^{10}$, $SZ^{10}$, and $NZ^{10}Z^{11}$;

$G^9$ is selected from the group consisting of O, S, —NH—NH—, and —N=N—;

$G^{10}$ is N or $CZ^{12}$;

$G^{11}$ is selected from the group consisting of $H_2N$, substituted $H_2N$, alkyl, substituted alkyl, aryl, and substituted aryl;

$Z^1$, $Z^6$, $Z^9$, and $Z^{11}$ are independently selected from the group consisting of H, alkyl, substituted alkyl, acyl, and substituted acyl;

$Z^2$ is selected from the group consisting of H, alkyl, substituted alkyl, aryl, substituted aryl, and heterocycle;

$Z^3$, $Z^5$, $Z^8$, and $Z^{10}$ are independently selected from the group consisting of H, alkyl, substituted alkyl, acyl, substituted acyl, aryl, and substituted aryl;

$Z^4$ is selected from the group consisting of alkyl, substituted alkyl, aryl, substituted aryl, and heterocycle;

$Z^7$ is selected from the group consisting of H, halogen, alkyl, substituted alkyl, aryl, substituted aryl, $OZ^8$, $SZ^8$, and $NZ^8Z^9$; and $Z^{12}$ is selected from the group consisting of H, halogen, alkyl, substituted alkyl, aryl, and substituted aryl;

with the proviso that when $R^1$ is

$G^1$, $G^2$, $G^3$, and $G^4$ cannot simultaneously have the following meanings:

$G^1$ and $G^2$=H, $G^3$=O, and $G^4$=H or $Z^2C=O$ where $Z^2$=alkyl, and with the proviso that when $R^1$ is

$G^1$, $G^2$, or $G^5$ cannot simultaneously have the following meanings: $G^1$ and $G^2$=H, and $G^5$=F;

or a pharmaceutically acceptable salt, solvate, clathrate, hydrate, or prodrug thereof; and (ii) one or more buffer components in an amount sufficient to reduce decomposition of the one or more compounds, or said pharmaceutically acceptable salt, solvate, clathrate, hydrate, or prodrug thereof.

63. The dispersible buffered tablet of claim 62 wherein said compound is

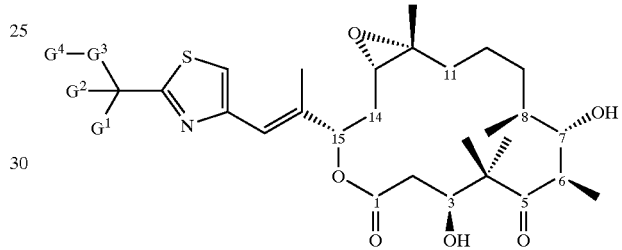

Ib wherein $G^1$, $G^2$, $G^3$, $G^4$, $Z^1$, $Z^2$, and $Z^3$ are as defined in claim 62.

64. The dispersible buffered tablet of claim 63 wherein said compound is [1S-[1R*,3R*(E),7R*, 10S*,11R*,12R*, 16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione.

* * * * *